US011337426B2

(12) United States Patent
Dagher et al.

(10) Patent No.: US 11,337,426 B2
(45) Date of Patent: May 24, 2022

(54) BIOLOGICAL CONTROL AGENTS AGAINST FIRE BLIGHT

(71) Applicant: Institut National De La Recherche Scientifique, Quebec (CA)

(72) Inventors: Fadi Dagher, Laval (CA); Eric Deziel, Rosemere (CA)

(73) Assignee: Institut National De La Recherche Scientifique, Quebec (CA)

( * ) Notice: Subject to any disclaimer, the term of this patent is extended or adjusted under 35 U.S.C. 154(b) by 1 day.

(21) Appl. No.: 16/706,514

(22) Filed: Dec. 6, 2019

(65) Prior Publication Data

US 2020/0178540 A1 Jun. 11, 2020

Related U.S. Application Data

(60) Provisional application No. 62/776,649, filed on Dec. 7, 2018.

(51) Int. Cl.

*A01N 63/20* (2020.01)
*C12N 1/20* (2006.01)
*A01N 63/22* (2020.01)
*A01N 63/27* (2020.01)

(52) U.S. Cl.

CPC ............. *A01N 63/20* (2020.01); *A01N 63/22* (2020.01); *A01N 63/27* (2020.01); *C12N 1/20* (2013.01)

(58) Field of Classification Search

None
See application file for complete search history.

(56) References Cited

U.S. PATENT DOCUMENTS

2010/0189798 A1 7/2010 Armstrong et al.
2018/0070586 A1* 3/2018 Kim ....................... A01N 25/22

FOREIGN PATENT DOCUMENTS

WO 2016/187703 A1 12/2016

OTHER PUBLICATIONS

Giddens et al. 2007 (Investigations into the in vitro antimicrobial activity and mode of action of the phenazine antibiotic D-alanylgriseoluteic acid; International Journal of Antimicrobial Agent 29: 93-97) (Year: 2007).*

Kim et al. 2012 (Controlled release of Pantoea agglomerans E325 for biocontrol of fire blight disease of apple; Journal of Controlled Release 161: 109-115). (Year: 2012).*

Giddens et al. 2002 (Characterization of a novel phenazine antibiotic gene cluster in Erwinia herbicola Eh1087; Mol Microbiol. 45(3) 769-783). (Year: 2002).*

BioSample: SAMN04990134; CFSAN: CFSAN034343, Pathogen: environmental/food/other sample from Paenibacillus polymyxa, 1 page [retrieved on Sep. 24, 2018 https://www.ncbi.nlm.nih.gov/biosample/?term=CFSAN034343].

BioSample: SAMN09909699; CFSAN: CFSAN047153, Pathogen: environmental/food/other sample from Pantoea agglomerans, 1 page [retrieved on Sep. 14, 2018 https://www.ncbi.nlm.nih.gov/biosample/9909699].

BioSample: SAMN09909698; CFSAN: CFSAN047154, Pathogen: environmental/food/other sample from Pantoea agglomerans, 1 page [retrieved on Sep. 14, 2018 https://www.ncbi.nlm.nih.gov/biosample/?term=CFSAN047154].

Fromin, N., et al., "The genotypic diversity of Pseudomonas brassicacearum populations isolated from roots of *Arabidopsis thaliana*: influence of plant genotype," FEMS Microbiology Ecology 37 21-29 (2001).

Granatstein, D., "Alternative Fire Blight Control Materials to Replace Antibiotics," Organic Tree Fruit Industry Work Group, 4 pages (2011).

Henry, D. A., et al., "Identification of Burkholderia cepacia Isolates from Patients with Cystic Fibrosis and Use of a Simple New Selective Medium," Journal of Clinical Microbiology, vol. 35, No. 3, p. 614-619 (1997).

Kim, In-Yong, et al., "Controlled release of Pantoea agglomerans E325 for biocontrol of fire blight disease of apple," Journal of Controlled Release 161, pp. 109-115 (2012).

Lenth, R. V., "Least-Squares Means: The R Package lsmeans," Journal of Statistical Software,, vol. 69, Issue 1 (2016).

Mitchell, R. E., et al., "An antibacterial pyrazole derivative from Burkholderia glumae, a bacterial pathogen of rice," Phytochemistry. vol. 69(15):2704-7 (2008).

Porter, J. N., et al., "Method for the Preferential Isolation of Actinomycetes from Soils," Biochemical Research Section, Lederle Laboratories, American Cyanamid Company, Pearl River, New York (1959).

Pusey, P. L., et al., "Antibiosis Activity of Pantoea agglomerans Biocontrol Strain E325 Against Erwinia amylovora on Apple Flower Stigmas," Phytopathology, vol. 101, No. 10, 1234-1241 (2011).

Roberts, D.C., et al., "Potential biological control of Erwinia tracheiphila by internal alimentary canal interactions in Acalymma vittatum with Pseudomonas fluorescens," Journal of Applied Microbiology ISSN 1364-5072 (2018).

Smits, T. H. M., et al., "Metabolic Versatility and Antibacterial Metabolite Biosynthesis Are Distinguishing Genomic Features of the Fire Blight Antagonist Pantoea vagans C9-1," Metabolism and Antibiotics of P. vagans 09-1,vol. 6 (7) e22247 (2011).

Stockwell, V. O., et al., "Control of Fire Blight by Pseudomonas fluorescens A506 and Pantoea vagans C9-1 Applied as Single Strains and Mixed Inocula," Phytopathology, vol. 100, No. 12, pp. 1331-1339 (2010).

(Continued)

*Primary Examiner* — Mary Maille Lyons
(74) *Attorney, Agent, or Firm* — Hamilton, Brook, Smith & Reynolds, P.C.

(57) ABSTRACT

Described herein are biopesticides having activity against *Erwinia* species, particularly against the fire blight phytopathogen *Erwinia amylovora*. The biopesticides comprise intact or vegetative cells, endospores, spores, and/or metabolites from one or more bacterial species or strains as active ingredients, wherein the vegetative cells, endospores, spores, and/or metabolites exhibit antimicrobial activity against phytopathogenic *Erwinia* species or *Erwinia amylovora*.

11 Claims, 8 Drawing Sheets

Specification includes a Sequence Listing.

(56) References Cited

OTHER PUBLICATIONS

Vrancken, K., "Pathogenicity and infection strategies of the fire blight pathogen Erwinia amylovora in Rosaceae: State of the art," Microbiology 159, pp. 823-832 (2013).
Wright et al.,"Pantoea agglomerans Strain EH318 Produces Two Antibiotics That Inhibit Erwinia amylovora In Vitro," Applied And Environmental Microbiology, vol. 67, No. 1, Jan. 2001. p. 284-292.
Stockwell et al., "Antibiosis Contributes to Biological Control of Fire Blight by Pantoea agglomerans Strain Eh252 in Orchards," Phytopathology, vol. 92, No. 11, 2002 p. 1202-1209.
Vanneste et al., "Presence of Genes Homologous to those Necessary for Synthesis of Microcin MccEh252 in Strains of Pantoea agglomerans," Proc. Xlth IW on Fire Blight, Eds.: K.B. Johnson and V.O. Stockwell, Acta Hort. 793, ISHS 2008, 6 pages.

* cited by examiner

Control (water only)

Inoculated (no treatment)

Inoculated + TSB

*P. agglomerans* NY60 only

Inoculated + *P. agglomerans* NY60

Streptomycin only

Inoculated + Streptomycin

Control (water only)

Inoculated (no treatment)

Inoculated + TSB

*P. agglomerans* NY60 only

Inoculated + *P. agglomerans* NY60

Streptomycin only

Inoculated + Streptomycin

BIOLOGICAL CONTROL AGENTS AGAINST FIRE BLIGHT

RELATED APPLICATION(S)

This application claims the benefit of U.S. Provisional Application No. 62/776,649, filed on Dec. 7, 2018. The entire teachings of the above application(s) are incorporated herein by reference.

The present invention relates to biological control agents having anti-microbial activity against the fire blight phytopathogen *Erwinia amylovora.*

The *Pantoea agglomerans* NY60 strain was deposited under accession number 190122-01 on Jan. 19, 2022 at International Depository Authority of Canada (IDAC) (National Microbiology Laboratory of Canada, 1015 Arlington Street, Winnipeg, Manitoba, Canada, R3E 3R2).

INCORPORATION BY REFERENCE OF MATERIAL IN ASCII TEXT FILE

This application incorporates by reference the Sequence Listing contained in the following ASCII text file being submitted concurrently herewith:

a) File name: 55911001000_Substitute_Sequence_Listing_02132020; created Feb. 14, 2020; 26,513 KB in size.

| SEQ ID NO: | Description |
|---|---|
| 1 | rpoB-f primer |
| 2 | rpoB-r primer |
| 3 | rpoB1698f primer |
| 4 | rpoB2041r primer |
| 5 | gyrA-f primer |
| 6 | gyrA-r primer |
| 7 | UP-1 primer |
| 8 | UP-2r primer |
| 9 | UP-1S primer |
| 10 | UP-2Sr primer |
| 11 | T7 primer |
| 12 | pA-27f-YM primer |
| 13 | pH primer |
| 14 | *P. agglomerans* NY60 chromosome |
| 15-18 | *P. agglomerans* NY60 plasmids 1-4 |
| 19 | *P. agglomerans* NY130 chromosome |
| 20-23 | *P. agglomerans* NY130 plasmids 1-4 |
| 24-103 | *P. poae* FL10F contigs 1-80 |
| 104-173 | *B. velezensis* FL50S contigs 1-70 |
| 174 | Tn-seq primer 1 |
| 175 | Tn-seq primer 2 |
| 176 | Tn-seq primer 3 |

The present application includes as part of its description a sequence listing that includes 176 sequences and this sequence listing is incorporated into the present application in its entirety.

BACKGROUND

Fire blight is a contagious disease affecting a number of agriculturally important crops such as apples, pears, and some other members of the Rosaceae family, and annual losses due to fire blight are significant in many countries. The bacterial plant pathogen responsible for fire blight is *Erwinia amylovora*, a rod-shaped Gram-negative bacterium capable of infecting different hosts in the Rosaceae family, including all species of the Maloideae subfamily.

While the most widely used formulations to control bacterial phytopathogens in crop protection are copper-based (e.g., copper hydroxide and copper sulphate), these formulations are not suitable for all plants because of phytotoxic effects, such as unacceptable rusting of the fruits of certain apple cultivars, and decreased fruit yields. Thus, the large-scale application of antibiotics (e.g., streptomycin and oxytetracycline) in agricultural fields have been widely used by growers to fight bacterial diseases, which has contributed to the rise of antibiotic resistant bacteria. In fact, antibiotics sprayed on apple and pear orchards were banned in some European countries to not only reduce the development of resistant bacteria, but also to eliminate the traces of antibiotics contaminating foods.

Presently, there are few effective biological products available to growers to fight diseases such as fire blight. Furthermore, some of the few biological products available were extensively tested as substitutes for antibiotics for more than 7 years in different regions of the United States, and they have generally been shown to have low efficacy and variability in results from one geography to another and from one year to the next (Granatstein, 2011). Thus, there is a need for effective and ecologically responsible products for controlling bacterial phytopathogens that cause fire blight and other plant diseases.

SUMMARY

Described herein are biopesticides having activity against *Erwinia* species, particularly *Erwinia amylovora*, the phytopathogen responsible for fire blight.

About 5,000 individual bacterial isolates from a total of 79 different North American environmental samples from a variety of geographic locations were collected, cultured and screened for potential direct antagonistic activity against *Erwinia amylovora*, based on their ability to produce inhibition zones on a lawn of *E. amylovora* 5435. Of the thousands of isolates screened, 205 candidate isolates were identified as exhibiting some degree of inhibition and cell-free supernatants from these 205 isolates were subsequently screened for potential activity of their extracellular metabolites. These screening efforts revealed a plurality of isolates whose undiluted cell-free supernatants exhibited anti-*Erwinia amylovora* activity, with cell-free supernatants from several isolates exhibiting activity even after 10-fold dilution. In fact, cell-free supernatants from several isolates even showed activity against streptomycin-resistant *E. amylovora*. Interestingly, the cell-free supernatants from several *Pantoea agglomerans* strains identified after initial screenings did not exhibit any detectable anti-*Erwinia amylovora* activity, but viable cells of these isolates exhibited potent anti-*Erwinia amylovora* activity, which in some cases were comparable to streptomycin treatment following in planta experiments on apple trees with minimal or no phytotoxicity observed. The identity of each of the active isolates was identified through DNA sequencing and other high-resolution taxonomic assignment methods/tools. Formulations of biopesticides comprising the active ingredients from the bacterial species/stains described herein were prepared having increased stability and/or shelf-life. Finally, the efficacy of selected biopesticides described herein were validated in field trials performed on McIntosh and Rome apple trees inoculated with *E. amylovora*, and compared to streptomycin treatment.

In some aspects, described herein is a biopesticide comprising intact or vegetative cells, endospores, spores, and/or metabolites from one or more bacterial species as active ingredients, wherein the vegetative cells, endospores, spores, and/or metabolites exhibit antimicrobial activity against phytopathogenic *Erwinia* species or *Erwinia amylovora*. In some embodiments, the one or more bacterial species may comprise spore-forming bacterial species, and/or the metabolites may comprise secondary and/or extracellular metabolites. In some embodiments, the one or more bacterial species may comprise or consist of: (a) a *Bacillus* species, a *Paenibacillus* species, a *Pantoea* species, a *Pseudomonas* species, or any combination thereof; (b) *Bacillus velezensis* (formerly known as *Bacillus amyloliquefaciens*), *Bacillus velezensis* subsp. *plantarum, Bacillus subtilis, Paenibacillus polymyxa, Pantoea agglomerans, Pseudomonas fluorescens, Pseudomonas poae*, or any combination thereof; (c) *Bacillus velezensis* 304, *Bacillus velezensis* 417, *Bacillus velezensis* 431, *Bacillus velezensis* subsp. *plantarum* FL50S, *Bacillus* sp. 331, *Bacillus* sp. 418, *Bacillus* sp. FD308, *Bacillus* sp. FD402, *Bacillus* sp. FD604, *Bacillus* sp. IRDA27, *Bacillus* sp. IRDA618, *Bacillus* sp. IRDA619, *Bacillus* sp. IRDA627, *Bacillus* sp. IRDA63, *Bacillus* sp. IRDA672, *Bacillus* sp. IRDA675, *Bacillus* sp. IRDA683, *Bacillus* sp. IRDA684, *Bacillus* sp. IRDA685, *Bacillus* sp. IRDA687, *Bacillus subtilis* 421, *Paenibacillus polymyxa* 273, *Paenibacillus polymyxa* 344, *Pantoea agglomerans* IRDA36, *Pantoea agglomerans* IRDA59, *Pantoea agglomerans* NY130, *Pantoea agglomerans* NY50, *Pantoea agglomerans* NY60, *Pseudomonas fluorescens* IRDA4, *Pseudomonas poae* FL10F, *Pseudomonas poae* FL3F, *Pseudomonas poae* FL4F, *Pseudomonas poae* FL9F, *Pseudomonas* sp. 41, *Pseudomonas* sp. 42, *Pseudomonas* sp. 43, *Pseudomonas* sp. NY1238, or any combination thereof; (d) *Pseudomonas poae, Bacillus velezensis* subsp. *plantarum, Paenibacillus polymyxa*, or any combination thereof; (e) *Pseudomonas poae* FL10F, *Pseudomonas poae* FL4F, *Pseudomonas poae* FL3F, *Bacillus velezensis* subsp. *plantarum* FL50S, *Paenibacillus polymyxa* 273, *Pseudomonas poae* FL9F, or any combination thereof; or (f) *Pantoea agglomerans* NY60 or *Pantoea agglomerans* NY130. In some embodiments, the one or more bacterial species comprise or consist of: (g) *Paenibacillus polymyxa, Bacillus velezensis* subsp. *plantarum, Pseudomonas poae, Pantoea agglomerans, Pantoea agglomerans, Pseudomonas fluorescens, Pseudomonas poae, Paenibacillus polymyxa, Bacillus velezensis* subsp. *plantarum*, or any combination thereof; and/or (h) *Paenibacillus polymyxa* 273, *Bacillus velezensis* subsp. *plantarum* FL50S, *Pseudomonas poae* FL10F, *Pantoea agglomerans* NY60, *Pantoea agglomerans* NY130, *Pseudomonas fluorescens* IRDA4, or any combination thereof.

In some embodiments, the biopesticide may comprise or consist of: (a) vegetative bacteria; (b) killed vegetative bacteria; (c) heat-killed vegetative bacteria; (d) sporulated bacteria; (e) bacterial spores or endospores; (f) bacterial extracellular metabolites; or (g) any combination thereof, from the one or more bacterial species as defined herein.

In some aspects, described herein is the use of the biopesticide as defined herein as an anti-microbial agent against a plant and/or human pathogenic microorganism, a phytopathogenic *Erwinia* species, *Erwinia amylovora*, or for the prevention and/or treatment of fire blight on a growing plant (e.g., a fruit plant, nut, cereal, vegetable, or flower).

In some aspects, described herein is a method for controlling the growth of a pathogenic microorganism on a target plant or tissue, the method comprising contacting the target plant or tissue with the biopesticide as defined herein.

In some aspects, described herein is a kit for preparing an aqueous solution for use in controlling a pathogenic microorganism (e.g. a phytopathogenic *Erwinia* species or *Erwinia amylovora*) on a plant tissue of a growing plant, the kit comprising: (a) the biopesticide as defined herein; and (b) a suitable container.

In some aspects, described herein is a method for producing the biopesticide as defined herein, the method comprising: for a biopesticide comprising spore-forming bacteria without vegetative cells as active ingredients, culturing vegetative cells from the one or more bacterial species in a sporulation medium for inducing sporulation; inactivating, heat-inactivating, or removing vegetative bacteria from the culture; or for a biopesticide comprising vegetative cells as active ingredients, culturing vegetative cells from the one or more bacterial species in a growth-promoting medium; and formulating the culture to improve viability.

In some aspects, described herein is a biopesticide comprising a vegetative *Pantoea agglomerans* strain as an active ingredient, wherein the vegetative *Pantoea agglomerans* strain: (a) is from the same subspecies as closely related *Pantoea agglomerans* strains NY60 (CFSAN047153) and NY130 (CFSAN047154); (b) has at least 90%, 91%, 92%, 93%, 94%, 95%, 96%, 97%, 98%, 99%, 99.5%, or 100% overall sequence identity at the genomic DNA level to CFSAN047153 and/or corresponding to the chromosomal sequence as set forth in SEQ ID NO: 14 and plasmids thereof (SEQ ID NOs: 15-18); and/or to CFSAN047154 and/or corresponding to the chromosomal sequence as set forth in SEQ ID NO: 19 and plasmids thereof (SEQ ID NOs: 20-23); (c) comprises genes encoding a bacteriocin, an aryl polyene, an acyl-homoserine lactone (hserlactone), a turnerbactin, a carotenoid, desferrioxamine B, a phenazine (e.g., pyocyanine and/or D-alanylgriseoluteic acid (AGA)), and a microcin; and/or (d) completely kills *E. amylovora* strains 5435, streptomycin-resistant 5153, and/or streptomycin-resistant S1605, when co-cultivated together in vitro.

In some aspects, described herein is a biopesticide comprising a live *Pseudomonas poae* strain and/or cell-free supernatant therefrom, as active ingredient, wherein the cell-free supernatant exhibits anti-*Erwinia amylovora* activity upon 10-fold dilution. In some embodiments, the *Pseudomonas poae* strain: (a) is from the same subspecies as *Pseudomonas poae* strain FL10F (CFSAN034337); (b) has at least 90%, 91%, 92%, 93%, 94%, 95%, 96%, 97%, 98%, 99%, 99.5%, or 100% overall sequence identity at the genomic DNA level to CFSAN034337 and/or corresponding to the contig sequences as set forth in any one of SEQ ID NOs: 24-103 or any combination thereof; and/or (c) comprises genes encoding a bacteriocin, an aryl polyene, a safracin, a pyoverdine, a mangotoxin, a poaeamide, a pyochelin, or any combination thereof.

In some aspects, described herein is a biopesticide comprising a live *Bacillus velezensis* strain and/or cell-free supernatant therefrom, as active ingredient, wherein the cell-free supernatant exhibits anti-*Erwinia amylovora* activity upon 10-fold dilution. In some embodiments, the *Bacillus velezensis* strain: (a) is from the same subspecies as *Bacillus velezensis* strain FL50SF (CFSAN034340); (b) has at least 90%, 91%, 92%, 93%, 94%, 95%, 96%, 97%, 98%, 99%, 99.5%, or 100% overall sequence identity at the genomic DNA level to CFSAN034340 and/or corresponding to contig sequences as set forth in any one of SEQ ID NOs: 104-173 or any combination thereof; and/or (c) comprises genes encoding difficidin, oxydifficidin, a bacteriocin, an aryl polyene, a macrolactin, a bacillaene, an iturin, a bacilysin, a surfactin, a bacillibactin, a fengycin, a plipastatin, a teichuronic acid, a locillomycin, a citrulline, or any combination thereof.

In some aspects, described herein is a method for manufacturing a biopesticide against fire blight, the method comprising: cultivating a bacterial strain which is the *Pantoea agglomerans* strain as defined herein, the *Pseudomonas poae* strain as defined herein, or the *Bacillus velezensis* strain as defined herein, under growth conditions; isolating active ingredients from the culture, the active ingredients comprising or consisting of intact or vegetative cells, endospores, spores, and/or metabolites from the bacterial species; and formulating the active ingredients for increased shelf-life, as compared to corresponding unformulated active ingredients.

General Definitions

The use of the word "a" or "an" when used in conjunction with the term "comprising" in the claims and/or the specification may mean "one" but it is also consistent with the meaning of "one or more", "at least one", and "one or more than one".

As used herein, the term "metabolites" refers to any compound, substance, or by-product obtainable by the culture or fermentation of a microorganism as described herein. In some embodiments, the metabolites of the present description may be produced by culturing microorganisms and harvesting extracellular metabolites produced therefrom (e.g., released into the culture supernatants). In other embodiments, the metabolites of the present description may be produced using recombinant DNA technology (e.g., recombinant proteins). In some embodiments, the metabolite may be a proteinaceous substance (i.e., a substance comprising a linear polymer chain of at least 3 amino acids bonded together by peptide bonds), bacteriocins, lantibiotics, lipopeptides and/or polyketides. In some embodiments, the metabolites may be extracellular bacterial and/or extracellular fungal secondary metabolites. As used herein, "secondary metabolites" refers to compounds that are not directly involved in normal growth, development, or reproduction. Unlike primary metabolites, the absence of secondary metabolites does not result in immediate death, but rather in long-term impairment of survivability, fecundity or aesthetics.

As used herein, the expression "antimicrobial" refers to the ability of the metabolites of the present description to prevent, inhibit, and/or destroy the growth of pathogenic microbes such as pathogenic bacteria and/or pathogenic fungi. In some embodiments, the expression "antimicrobial" encompasses agents or compounds exhibiting antagonistic activity against pathogenic microbes. In some embodiments, the antimicrobial activity may be in vitro antimicrobial activity or in vivo antimicrobial activity.

In some embodiments, the present description relates to metabolites having antimicrobial activity against phytopathogenic *Erwinia* species, particularly *Erwinia amylovora*. As used herein, term "pathogen" or "pathogenic" refers to an organism capable of producing a disease in a plant or animal. The term "phytopathogen" as used herein refers to a pathogenic organism that infects a plant.

In some embodiments, the present description relates to metabolites which may be extracellular bacterial metabolites. As used herein, the term "extracellular" refers to the compounds that are secreted or released (either actively or passively) into the extracellular medium upon culture of viable cells, but may also include compounds that contact the extracellular medium, but which remain associated with the cell membrane.

In some embodiments, the present description relates to metabolites from a *Bacillus* species, a *Paenibacillus* species, a *Pantoea* species, a *Pseudomonas* species, or any combination thereof. As used herein, the expression "from a [genus] species" or "obtainable from a [genus] species", refers to a compound that may be obtained (i.e., that is obtainable) from the culture or fermentation of a species belonging to the recited genus, but does not necessarily mean that the metabolite must be obtained from that particular species or from the culture of a microorganism per se. For example, compounds produced recombinantly or synthetically, but which have a structure substantially corresponding to the metabolite from the recited species, are also encompassed in the aforementioned expressions. In contrast, as used herein, the expression "produced from" is intended to refer to a compound which is obtained from the culture or fermentation of a microorganism of the present description.

In some embodiments, the compositions described herein may be used as an anti-microbial (e.g., bactericidal and/or fungicidal) agent against a plant and/or human pathogenic microorganism, or for the manufacture of an anti-microbial agent for same. In some embodiments, the pathogenic microorganism may be a phytopathogenic *Erwinia* species, particularly *Erwinia amylovora*. In some embodiments, antimicrobial compositions, bacterial species/strains described herein may be used for biological control. As used herein, the expression "biological control" refers to the control of a pathogen or any other undesirable organism by the use of at least a second organism other than man. In some embodiments, the compositions defined herein may be a biopesticide or biological pesticide. As used herein, the expressions "biopesticide" and "biological pesticide" refer to non-naturally occurring commercial products that may include naturally occurring metabolites/microorganisms which are formulated to have anti-microbial activity when applied to plants. Such formulations increase the stability and/or concentrations of the metabolites/microorganisms to levels that are not found in nature, which enable them to be useful as plant pesticides.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

In the appended drawings:

FIG. 2A: One milliliter sterile water (no inoculation). FIG. 2B: One milliliter *E. amylovora* S1605 at $OD_{620}$=0.2. FIG. 2C: One milliliter *E. amylovora* S1605 at $OD_{620}$=0.2, followed by 1 mL of Tryptic Soy Broth (TSB) medium 30 min later. FIG. 2D: One milliliter *P. agglomer-*

*ans* NY60 ($OD_{620}$=0.2) only. FIG. 2E: One milliliter *E. amylovora* S1605 at $OD_{620}$=0.2, followed by 1 ml NY60 culture ($OD_{620}$=0.2) 30 min later. FIG. 2F: One milliliter sterile water containing 100 ppm streptomycin. FIG. 2G: One milliliter *E. amylovora* S1605 at $OD_{620}$=0.2, followed by 1 mL sterile water containing 100 ppm streptomycin 30 min later.

FIG. 3A: One milliliter sterile water (no inoculation). FIG. 3B: Apple leaves cut with sterile scissors inoculated with 1 mL *E. amylovora* S1605 ($OD_{620}$=0.2). FIG. 3C: Apple leaves cut with sterile scissors inoculated with 1 mL *E. amylovora* S1605 ($OD_{620}$=0.2) followed by 1 mL TSB 30 min later. FIG. 3D: Apples leaves treated with 1 mL strain *P. agglomerans* NY60 ($OD_{620}$=0.2). FIG. 3E: Apple leaves cut with sterile scissors inoculated with 1 ml *E. amylovora* S1605 ($OD_{620}$=0.2), then treated with 1 mL strain *P. agglomerans* NY60 ($OD_{620}$=0.2) 30 min later. FIG. 3F: Apple leaves injected with 1 mL sterile water containing 100 ppm streptomycin. FIG. 3G: Apple leaves cut with sterile scissors inoculated with 1 mL *E. amylovora* S1605 ($OD_{620}$=0.2) then treated with 1 mL sterile water containing 100 ppm streptomycin 30 min later.

FIG. 4A: surfactins detected in positive ionization mode. FIG. 4B: iturins detected in positive ionization mode. FIG. 4C: fengycins detected in positive ionization mode. In the case of fengycins, peaks correspond to the doubly charged ions.

DETAILED DESCRIPTION

Figure 1A:
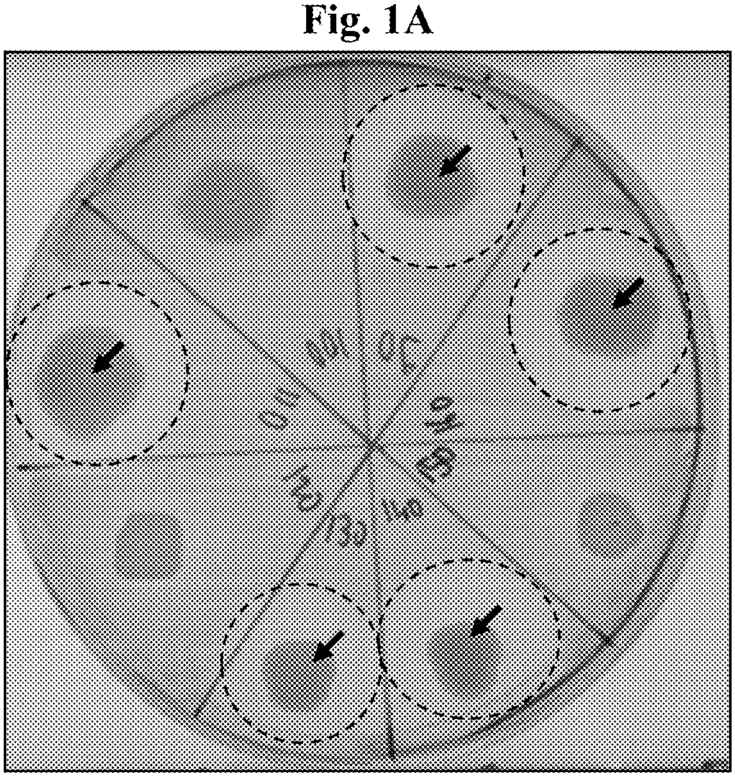
FIG. 1A shows the antagonistic activity of several active bacterial isolates against *E. amylovora* 5435. Bacterial isolates such as those indicated with arrows were selected because they formed clear haloes (inhibition zones indicated by dotted circles) around their colonies on an *E. amylovora* 5435 lawn.

In some aspects, described herein is a biopesticide comprising active ingredients from one or more bacterial species and/or strains that exhibit antimicrobial activity against phytopathogenic *Erwinia* species, particularly against *Erwinia amylovora*, the bacterial plant pathogen responsible for fire blight.

In some embodiments, the one or more bacterial species and/or strains described herein may comprise or consists of: (a) bacteria from the genus *Bacillus, Paenibacillus, Pantoea, Pseudomonas*, or any combination thereof; (b) bacteria from the species *Bacillus velezensis* (i.e. *Bacillus amyloliquefaciens*), *Bacillus velezensis* subsp. *plantarum, Bacillus subtilis, Paenibacillus polymyxa, Pantoea agglomerans, Pseudomonas fluorescens, Pseudomonas poae*, or any combination thereof; or (c) the bacterial strains *Bacillus velezensis* 304, *Bacillus velezensis* 417, *Bacillus velezensis* 431, *Bacillus velezensis* subsp. *plantarum* FL50S, *Bacillus* sp. 331, *Bacillus* sp. 418, *Bacillus* sp. FD308, *Bacillus* sp. FD402, *Bacillus* sp. FD604, *Bacillus* sp. IRDA27, *Bacillus* sp. IRDA618, *Bacillus* sp. IRDA619, *Bacillus* sp. IRDA627, *Bacillus* sp. IRDA63, *Bacillus* sp. IRDA672, *Bacillus* sp. IRDA675, *Bacillus* sp. IRDA683, *Bacillus* sp. IRDA684, *Bacillus* sp. IRDA685, *Bacillus* sp. IRDA687, *Bacillus subtilis* 421, *Paenibacillus polymyxa* 273 (also referred to as *Paenibacillus peoriae* 273), *Paenibacillus polymyxa* 344, *Pantoea agglomerans* IRDA36, *Pantoea agglomerans* IRDA59, *Pantoea agglomerans* NY130, *Pantoea agglomerans* NY50, *Pantoea agglomerans* NY60, *Pseudomonas fluorescens* IRDA4, *Pseudomonas poae* FL10F, *Pseudomonas poae* FL3F, *Pseudomonas poae* FL4F, *Pseudomonas poae* FL9F, *Pseudomonas* sp. 41, *Pseudomonas* sp. 42, *Pseudomonas* sp. 43, *Pseudomonas* sp. NY1238, or any combination thereof. Bacteria from the above-mentioned genera/species/strains were found to produce inhibition zones on a lawn on *E. amylovora* after screenings for antimicrobial activity of cell-free supernatants (see Tables 3 and 4) and/or direct antagonistic activity (see Table 5), as described in Example 2.

In some embodiments, the one or more bacterial species and/or strains described herein may comprise or consists of: (d) bacteria from the species *Pseudomonas poae, Bacillus velezensis* subsp. *plantarum, Paenibacillus polymyxa*, or any combination thereof; or (e) bacteria from the strains *Pseudomonas poae* FL10F, *Pseudomonas poae* FL4F, *Pseudomonas poae* FL3F, *Bacillus velezensis* subsp. *plantarum* FL50S, *Paenibacillus polymyxa* 273, *Pseudomonas poae* FL9F, or any combination thereof. Cell-free supernatants from the above-mentioned species/strains were found to produce inhibition zones on a lawn on *E. amylovora* even following a 10-fold dilution, as shown in Table 3.

In some embodiments, the one or more bacterial species and/or strains described herein may comprise or consists of: (f) bacteria from the strains *Pantoea agglomerans* NY60 or *Pantoea agglomerans* NY130. Strikingly, these strains were the only ones that exhibited the ability of completely killing *E. amylovora* strains S435, streptomycin-resistant S153, and streptomycin-resistant S1605 when co-cultivated together in vitro, as described in Examples 1.8 and 5. Such effective inhibitory activity of *P. agglomerans* against *E. amylovora* is not believed to have been previously reported (Pusey et al., 2011; Smits et al., 2011; Stockwell et al., 2010; Kim et al., 2012), and is particularly unexpected because, for example, of the inactivity of their extracellular metabolites against *E. amylovora* (see Table 3).

In some embodiments, the one or more bacterial species and/or strains described herein may comprise or consists of: (g) bacteria from *Paenibacillus polymyxa, Bacillus velezensis* subsp. *plantarum, Pseudomonas poae, Pantoea agglomerans, Pantoea agglomerans, Pseudomonas fluorescens, Pseudomonas poae, Paenibacillus polymyxa, Bacillus velezensis* subsp. *plantarum*, or any combination thereof; and/or (h) bacteria from the strains *Paenibacillus polymyxa* 273, *Bacillus velezensis* subsp. *plantarum* FL50S, *Pseudomonas poae* FL10F, *Pantoea agglomerans* NY60, *Pantoea agglomerans* NY130, *Pseudomonas fluorescens* IRDA4, or any combination thereof. These species/strains were shown to be amendable to formulation for improved shelf-life, as described in Example 6. Furthermore, the cell-free supernatants from *Pseudomonas poae* FL10F, *Paenibacillus polymyxa* 273, *Bacillus velezensis* subsp. *plantarum FL50S*, *Pseudomonas*, demonstrated the strongest antimicrobial activity against three different *E. amylovora* strains, including two streptomycin-resistant strains.

In some embodiments, one or more bacterial species and/or strains described herein may comprise or consists of the following strains: *Paenibacillus polymyxa* 273, which is the strain corresponding to the Center for Food Safety and Applied Nutrition (CF SAN) strain CFSAN034343, BioSample: SAMN04990134, GenBank assembly accession: GCA_001707685.1, Genbank assembly name: ASM170768v1, GenBank sequence accession no: NZ_LYND01000206; *Pseudomonas* pose FL10F, which is the strain corresponding to CFSAN strain CFSAN034337 and/or corresponding to the contig sequences as set forth in any one of SEQ ID NOs: 24-103 or any combination thereof; *Pseudomonas* pose FL9F, which is the strain corresponding to CF SAN strain CFSAN055119; *Pseudomonas* pose FL3F, which is the strain corresponding to CF SAN strain CFSAN034336; Fluorescent *Pseudomonas* spp. IRDA4, which is the strain corresponding to CF SAN strain CFSAN055120; *Bacillus velezensis* FL50S which is the strain corresponding to CFSAN strain CFSAN034340 and/or corresponding to contig sequences as set forth in any one of SEQ ID NOs: 104-173 or any combination thereof; *Pantoea agglomerans* NY60, which is the strain corresponding to CFSAN strain CFSAN047153, BioSample: SAMN09909699 and/or corresponding to the chromosomal sequence as set forth in SEQ ID NO: 14 and plasmids thereof (SEQ ID NOs: 15-18); or *Pantoea agglomerans* NY130, which is the strain corresponding to CFSAN strain CFSAN047154, BioSample: SAMN09909698 and/or corresponding to the chromosomal sequence as set forth in SEQ ID NO: 19 and plasmids thereof (SEQ ID NOs: 20-23). In some embodiments, the one or more bacterial species and/or strains described herein may comprise or consists of a strain (e.g. a subspecies) having at least 90%, 91%, 92%, 93%, 94%, 95%, 96%, 97%, 98%, 99%, 99.5%, or 100% overall sequence identity at the genomic DNA level to one of the strains identified herein by a public CF SAN strain number and/or GenBank accession number.

In some embodiments, a *Pseudomonas poae* strain described herein may comprise native genomic and/or recombinantly-introduced genes encoding one or more of the metabolites a bacteriocin, an aryl polyene, a safracin, a pyoverdine, a mangotoxin, a poaeamide, a pyochelin, and a tolaasin; preferably a bacteriocin, an aryl polyene, a safracin, a pyoverdine, a mangotoxin, a poaeamide, a pyochelin, or any combination thereof.

In some embodiments, a Fluorescent *Pseudomonas* spp. strain described herein may comprise native genomic and/or recombinantly-introduced genes encoding one or more of the metabolites a bacteriocin, an aryl polyene, a safracin, a pyoverdine, a mangotoxin, a poaeamide, a pyochelin, a syringafactin, or any combination thereof.

In some embodiments, a *Pantoea agglomerans* strain described herein may comprise native genomic and/or recombinantly-introduced genes encoding one or more of the metabolites a bacteriocin, an aryl polyenes, an acyl homoserine lactone, a turnerbactin, a carotenoid, desferrioxamine B, a phenazine (e.g., pyocyanine and/or D-alanylgriseoluteic acid (AGA)), a microcin, or any combination thereof.

In some embodiments, a *Bacillus velezensis* strain herein may comprise native genomic and/or recombinantly-introduced genes encoding one or more proteins involved in the synthesis, upregulation, or extra-cellular export of difficidin, oxydifficidin, a bacteriocin, an aryl polyene, a macrolactin, a bacillaene, an iturin, a bacilysin, a surfactin, a bacillibactin, a fengycin, a plipastatin, a teichuronic acid, a locillomycin, a citrulline, or any combination thereof.

As used in the context of biopesticides described herein, the expression "active ingredient" refers mainly to bacteria-derived agents that are present in sufficient concentrations and formulated to possess the desired antimicrobial activity (e.g., against *Erwinia* species, particularly against *Erwinia amylovora*). In some embodiments, the active agents may include intact cells (e.g., live vegetative cells, sporulated bacteria), killed vegetative bacteria (e.g., heat-killed vegetative bacteria), bacterial endospores/spores (e.g., heat-treated endospores/spores), metabolites (e.g., primary, secondary, intracellular, extracellular/secreted metabolites), or any combination thereof, from one or more bacterial species or strains described herein that exhibit antimicrobial activity against *Erwinia amylovora*. In some embodiments, the active ingredients are obtainable from or produced by a bacterial species/strain described herein.

In some embodiments, the biopesticide described herein may comprise active agents from one or more spore-forming bacterial species described herein (e.g., *P. polymyxa, B. velezensis* subsp. *plantarum*). For example, the biopesticide may be prepared as described in Example 1.11 by culturing the spore-forming bacteria in a sporulation medium (e.g., Schaeffer's sporulation medium) under conditions (e.g., temperature, time, and agitation conditions) to achieve the desired level of sporulation. The cultures may then be heated at a temperature and for a sufficient period of time to inactivate or kill substantially all vegetative bacteria in the culture, thereby producing a product devoid of vegetative bacteria that comprises spores and/or metabolites (e.g., extracellular metabolites) as active ingredients. In some embodiments, biopesticides lacking live, vegetative bacteria may present advantages in terms of product storage, shelf-life, as well as more favorable paths for regulatory approval.

In some embodiments, the biopesticides described herein may comprise live vegetative bacteria from one or more bacterial species/strains described herein as an active ingredient. Such biopesticide formulations may be advantageous particularly for bacterial species/strains that exhibit their antimicrobial activity via direct antagonism and/or competition (e.g., as shown in Table 5 for various *Pantoea agglomerans* strains such as NY50, NY60, NY130, IRDA36, and IRDA59; and in Example 5), and/or bacteria that produce/secrete antimicrobial extracellular metabolites. Such vegetative bacteria-containing biopesticide formulations may also be advantageous to achieve, for example, longer-lasting products that can colonize, compete with *E. amylovora*, and/or provide extended protection to target plants susceptible to fire blight or other diseases. Indeed, candidate bacteria in the present study were isolated from the flowers, leaves, and soil in apple- and pear orchards from springtime bloom to the summer season. In this way, the likelihood of isolating bacteria capable of colonizing the trees and competing against *E. amylovora* would be optimized.

In some embodiments, the biopesticides described herein may comprise live vegetative bacteria from one or more bacterial species/strain described herein as an active ingredient, wherein the live vegetative bacteria have a functional type VI secretion system. Without being bound by theory, such systems may be mainly responsible for interbacterial antagonism (e.g., for *P. agglomerans*).

In some embodiments, the biopesticides described herein may comprise live vegetative bacteria from only one bacterial species/strain described herein (or in total) as an active ingredient. Such biopesticide formulations may be advantageous particularly for bacterial species/strains that show antagonism not only with *E. amylovora*, but also with other antimicrobial (e.g., anti-*Erwinia*) bacterial species/strains.

Furthermore, a biopesticide comprising only a single bacterial species/strain as an active ingredient may be easier and/or less costly to produce and formulate that biopesticides comprising combinations of different bacterial species/strains.

In some embodiments, preparation of such formulation may comprise a step of culturing the one or more bacterial species under conditions to promote or increase production of secondary metabolites and/or extracellular metabolites (e.g., as compared to under standard growth conditions). For example, the one or more bacterial species are cultured in the presence of glycerol (e.g., about 0.5% w/w) to promote production of extracellular metabolites. Accordingly, the biopesticides described herein may comprise glycerol.

In some embodiments, the cultures comprising live vegetative bacteria and their metabolites may be treated (e.g., heated) to kill remaining vegetative bacteria, leaving the metabolites as active ingredients. As mentioned above, biopesticides lacking live, vegetative bacteria may present advantages in terms of product storage, shelf-life, as well as more favorable paths for regulatory approval. In some embodiments, the intact or vegetative cells may be removed (e.g., via centrifugation and/or filtration) to obtain a cell-free product.

In some embodiments, the biopesticides described herein may comprise one or more agriculturally-suitable additives or preservatives for increased stability/shelf-life. For example, one or more agriculturally-suitable salts may be added as a preservative (e.g., NaCl at about 4% w/w).

In some embodiments, the biopesticides described herein may comprise more than one type of active ingredients (e.g., vegetative bacteria, sporulated bacteria, endospores/spores, and/or extracellular metabolites) and/or active ingredients originating from at least two, at least three, at least four, at least five, at least six, at least seven, at least eight, at least nine, or at least ten different bacterial species/strains described herein. In some embodiments, the combination use of different types of active ingredients and/or from different bacterial species may reduce the likelihood that the pathogenic microorganism (e.g., *E. amylovora*) develops resistance.

In some embodiments, the biopesticides described herein may lack (not comprise) vegetative bacteria as an active ingredient or is a cell-free composition; and may comprise bacterial spores or endospores, and/or bacterial extracellular metabolites from one or more bacterial species as defined herein, as active ingredients. Alternatively, in some embodiments, the biopesticides described herein may comprise vegetative bacteria (and extracellular metabolites) from the one or more bacterial species as defined herein, as active ingredients. In some embodiments, biopesticides described herein comprise vegetative *Pantoea agglomerans, Pantoea agglomerans* NY50, *Pantoea agglomerans* NY60, *Pantoea agglomerans* NY130, *Pantoea agglomerans* IRDA36, *Pantoea agglomerans* IRDA59, or any combination thereof, as active ingredients.

In some embodiments, the biopesticides described herein may comprise active ingredients (e.g., cells, spores, metabolites) from a microorganism that is naturally-occurring and/or that has not been genetically modified using recombinant DNA technology, and thus qualifies as a natural biopesticide and/or natural bioproduct. In alternative embodiments, the biopesticides described herein may comprise active ingredients (e.g., cells, spores, metabolites) from a microorganism that is or has been genetically modified using recombinant DNA technology, for example to improve efficacy and/or stability. In some embodiments, the active ingredients (e.g., cells, spores, metabolites) may be from a mutant microorganism derived from a bacterial species/strain described herein, wherein the mutant retains anti-*Erwinia amylovora* activity.

In some embodiments, the present description relates to genetically modified or mutant antimicrobial bacterial or fungal strains as defined herein. As used herein, the term "mutant" making reference to a microorganism refers to a modification of the parental strain in which the desired biological activity (e.g., ability to produce antimicrobial metabolites as defined herein) is similar to or higher than that expressed by the parental strain.

In some embodiments, the biopesticides described herein have the ability to completely kill *Erwinia amylovora* S453, *Erwinia amylovora* S153, *Erwinia amylovora* S1605, or any combination thereof, when co-cultured together in vitro (e.g., as described in Example 5).

In some embodiments, the biopesticides described herein may exhibit antimicrobial activity against a further plant and/or human pathogenic microorganism, or a pathogenic virus, bacteria, fungus, yeast, mold, or any combination thereof. In some embodiments, biopesticides described herein may have broad spectrum antimicrobial activity. In some embodiments, the biopesticides described herein may exhibit higher antimicrobial activity against *Erwinia* species (e.g., *Erwinia amylovora*), as compared to other phytopathogenic species.

In some embodiments, biopesticides described herein may comprise at least one, at least two, at least three, at least four, at least five, at least six, at least seven, at least eight, at least nine, or at least ten different bacterial metabolites (e.g., secondary metabolites and/or extracellular metabolites). In some embodiments, the metabolites may comprise lipopeptides and/or siderophores from the one or more bacterial species as defined herein. In some embodiments, the metabolites may comprise metabolites selected from non-ribosomal lipopeptides (NRPs), bananamide, poaeamide, poacin, viscosin, massetolide, orfamide, arthrofactin, surfactin, fengycin, plipastatin, iturin, bacilysin, bacillibactin, bacillomycin, locillomycin, paenilarvin, pelgipeptin, polymyxin, paenibacterin, fusaricidin, bacitracin, tridecaptin, bacteriocin, arylpolyene, acyl homoserine lactone (hserlactone), turnerbactin, carotenoid, desferrioxamine B, pyocyanine, microcin, pantocin, safracin, pyoverdine, mangotoxin, pyochelin, tolaasin, syringafactin, or any combination thereof.

In some embodiments, biopesticides described herein may comprise one or more polyketides. In some embodiments, polyketides could comprise difficidin and/or oxydifficidin. In some embodiments, said polyketides can be oxidized and/or dephosphorylated. In some embodiments, said polyketides may be from one or more bacterial species described herein. In some embodiments, said polyketides may be from *B. velezensis* FL50S.

In some embodiments, biopesticides described herein may comprise isolated, purified, or enriched oxydifficidin (e.g., as the major or principal against against phytopathogenic *Erwinia* species (e.g., *Erwinia amylovora*). In some embodiments, the levels of oxydifficidin in the biopesticides described herein may be present at levels or concentrations that do not occur in nature. In some embodiments, biopesticides described herein may comprise a fraction of cell-free supernatant comprising concentrated oxydifficidin, and optionally lower levels of difficidin. In some embodiments, a cell-free supernatant (or fraction thereof) comprising difficidin may be subjected to an oxidation reaction to convert the difficidin to oxydifficidin, thereby producing a composition comprising increased oxydifficidin. In some embodiments, the present description relating to oxydifficidin may comprise chemical variants of oxydifficidin (e.g., dephosphorylated oxydifficidin).

In some embodiments, biopesticides described herein may comprise one or more lipopeptides. In some embodiments, said lipopeptides could be cyclic lipopeptides. In some embodiments, biopesticides described herein may comprise one or more lipopeptides from the viscosin subfamily, such as white-line-inducing principle (WLIP), massetolide E, massetolide F, massetolide L, viscosin, or any combination thereof. In some embodiments, said cyclic lipopeptides comprise massetolide and/or viscosin. In some embodiments, said massetolide and/or viscosin is white line-inducing principle (WLIP). In some embodiments, said cyclic lipopeptides may be from one or more bacterial species described herein. In some embodiments, said cyclic lipopeptides may be from *P. poae* FL10F.

In some embodiments, biopesticides described herein may comprise one or more metabolites, antibiotics, or proteins involved in the synthesis and/or release of antibiotics. In some embodiments, the antibiotic is a phenazine. In some embodiments, the phenazine is D-alanylgriseoluteic acid (AGA). In some embodiments, said protein involved in the synthesis and/or release of antibiotics is the bacterial protein EhpJ. In some embodiments, said metabolites, antibiotics, or proteins may be from one or more bacterial species described herein. In some embodiments, said metabolites, antibiotics, or proteins may be from *P. agglomerans* NY60 or NY130.

In some embodiments, biopesticides described herein may comprise an agriculturally acceptable excipient, additive, and/or preservative (e.g., non-toxic carriers, surfactants, preservatives, nutrients, UV protectants, stickers, spreaders, and chelating agents). As used herein, the phrase "agriculturally acceptable excipient" refers to an essentially inert substance that can be used as a diluent and/or carrier for an active agent (e.g., antimicrobial metabolites of the present description) in a composition or biopesticide for treatment of plants.

In some embodiments, biopesticides described herein may be formulated as a liquid, concentrate, powder, tablet, gel, pellets, granules, or any combination thereof.

In some embodiments, biopesticides described herein, once applied to a target plant, may have no detectable phytotoxic effect on said target plant, or on the fruits, nuts, or leaves thereof.

In some embodiments, the biopesticides described herein comprise effective amounts of each active ingredient. An "effective amount", as used herein, is an amount sufficient to effect beneficial or desired results. An effective amount can be administered in one or more administrations. In terms of treatment, inhibition or protection, an effective amount is that amount sufficient to ameliorate, stabilize, reverse, slow or delay progression of the target infection or disease states.

In some embodiments, biopesticides described herein may comprise one or more active ingredients at concentrations of at least about 100 ppm, 200 ppm, 300 ppm, 400 ppm, 500 ppm, 600 ppm, 700 ppm, 800 ppm, 900 ppm, 1000 ppm, 1500 ppm, 2000 ppm, 2500 ppm, 3000 ppm, 3500 ppm, 4000 ppm, 4500 ppm, 5000 ppm, 5500 ppm, 6000 ppm, 6500 ppm, 7000 ppm, 8000 ppm, 8500 ppm, 9000 ppm, 9500 ppm, or 10 000 ppm. In some embodiments, biopesticides described herein may comprise one or active ingredients at concentrations of between about 100 ppm, 200 ppm, 300 ppm, 400 ppm, 500 ppm, 600 ppm, 700 ppm, 800 ppm, 900 ppm, 1000 ppm, 1500 ppm, 2000 ppm, 2500 ppm, 3000 ppm, 3500 ppm, 4000 ppm, 4500 ppm, 5000 ppm, to about 10 000 ppm. The term "about" is used herein to indicate that a value includes the standard deviation of error for the device or method being employed to determine the value. In general, the terminology "about" is meant to designate a possible variation of up to 10%. Therefore, a variation of 1, 2, 3, 4, 5, 6, 7, 8, 9 and 10% of a value is included in the term "about".

In some embodiments, biopesticides described herein are for use as an anti-microbial agent against a plant and/or human pathogenic microorganism, a phytopathogenic *Erwinia* species, *Erwinia amylovora*, or for the prevention and/or treatment of fire blight on a growing plant. In some embodiments, the present description relates to the use of the biopesticide as defined herein as an anti-microbial agent against a plant and/or human pathogenic microorganism, a phytopathogenic *Erwinia* species, *Erwinia amylovora*, or for the prevention and/or treatment of fire blight on a growing plant. In some embodiments, the growing plant is a fruit plant, nut, cereal, vegetable, or flower. In some embodiments, the fruit is pome fruit trees and related plants, Pear (*Pyrus* species), quince (*Cydonia*), apple, crabapple (*Malus* species), firethorns (*Pyracantha* species), hawthorn (*Crataegus* species), *Spiraea, Cotoneaster*, toyon (*Photinia* species), juneberry, serviceberry (*Amelanchier* species), loquat (*Eriobotria*), mountain ash (*Sorbus* species), blossom (*Prunus*) peach, apricot, cherry, banana, blackberry, blueberry, cantaloupe, cherry, cranberry, currant, grapes, greengage, gooseberry, honeydew, lemon, mandarin, melon, orange, peach, pears, pineapple, plum, raspberry, strawberry, tomatoes, watermelon, grapefruit, pepper, olive, or lime; the nut is: almond, beech nut, Brazil nut, butternut, cashew, chestnut, chinquapin, filbert, hickory nut, macadamia nut, pecan, walnut, or pistachio; the cereal is: amaranth, breadnut, barley, buckwheat, canola, corn, fonio, kamut, millet, oats, *quinoa*, cattail, chia, flax, kañiwa, pitseed goosefoot, wattleseed, rice, rye, sorghum, spelt, teff, triticale, wheat, or colza; the vegetable is: artichoke, bean, beetroot, broad bean, broccoli, cabbage, carrot, cauliflower, celery, chicory, chives, cress, cucumber, kale, dill, eggplant, kohlrabi, lettuce, onion, pepper, parsnip, parsley, pea, potato, pumpkin, radish, shallot, soybean, spinach, turnip, or peanut; or the growing plant is an apple tree, pear tree, an apricot plant, stone fruit tree, a plant from the rose family (Rosaceae family, or the Maloideae subfamily).

In some aspects, described herein is a method for controlling the growth of a pathogenic microorganism on a target plant or tissue, the method comprising contacting said target plant or tissue with the biopesticide as defined herein in sufficient/effective amounts to achieve the desired antimicrobial effect. In some embodiments, the pathogenic microorganism is a phytopathogenic *Erwinia* species or *Erwinia amylovora*. In some embodiments, the contacting method comprises spraying, irrigating, painting, daubing, and/or fogging, onto and/or into the target plant or tissue, the target plant or tissue's hydroponic substrate, and/or the target plant or tissue's agricultural earth (e.g., a growing plant as defined herein).

In some aspects, described herein is a kit for preparing an aqueous solution for use in controlling a pathogenic microorganism (e.g., a phytopathogenic *Erwinia* species or *Erwinia amylovora*) on a plant tissue of a growing plant, the kit comprising a biopesticide as defined herein; and a suitable container (e.g., a pouch, a tablet, or bucket).

In some aspects, described herein is a method for producing the biopesticide as defined herein. For a biopesticide comprising spore-forming bacteria without vegetative cells as active ingredients, the method may comprise culturing vegetative cells from the one or more bacterial species/strain described herein in a sporulation medium for inducing sporulation; and inactivating, heat-inactivating, or removing vegetative bacteria from the culture. For a biopesticide comprising vegetative cells as active ingredients, The method may comprise culturing vegetative cells from the one or more bacterial species/strain described herein in a growth-promoting medium; and formulating the culture to improve viability. In some embodiments, the aforementioned methods may further comprise culturing the one or more bacterial species/strains described herein under conditions to promote production of secondary metabolites and/or extracellular metabolites (e.g., in the presence of glycerol, such as about 0.5% w/w glycerol). In some embodiments, the method may further comprise adding a preservative, additive or stabilizer to improve the shelf-life of the active ingredients. In some embodiments, the method may comprise combining one or more active ingredients from at least two, at least three, at least four, at least five, at least six, at least seven, at least eight, at least nine, or at least ten different bacterial species/strains described herein.

EXAMPLES

Example 1: Materials and Methods 1.1 Media

Two nonselective media (Tryptic Soy Agar (TSA), and Plate Count Agar (PCA)) and three selective media (Benedict, for isolation of *Streptomyces* spp., Porter et al., 1960; BCSA, for isolation of *Burkholderia* spp., Henry et al., 1997); and Gould, for isolation of *Pseudomonas* spp., Fromin et al., 2001) supplemented with 50 mg/mL cycloheximide (to limit the growth of fungi) were used to isolate bacteria from environmental samples.

1.2 Isolation of Microorganisms from Plants

Ten seeds and three segments (0.5 $cm^2$) randomly excised from each leaf, stem, root, and fruit were vortexed in 5 mL sterile 0.85% (w/w) NaCl. To isolate sporulating bacteria, the suspensions were preheated at 80° C. for 30 min. Aliquots (100 μL) of each suspension were spread onto the nonselective- and selective media plates. To isolate bacteria, the plates were incubated in the dark for 2-5 days at room temperature (~21° C.). Microorganisms were isolated from plant samples in triplicate.

1.3 Isolation of Bacteria from Soil

One gram of soil was added to 9 mL sterile phosphate-buffered saline (PBS) then agitated for 30 min. Sample suspensions were serially diluted. One hundred microliters of each dilution ($10^{-2}$, $10^{-3}$, and $10^{-4}$) were spread onto nonselective- and selective media. Plates were incubated under the same conditions as above. This assay was performed in triplicate.

1.4 Storage and Culture of Isolated Bacteria

Colonies of bacteria were purified first and then colonies with different morphological characteristics were transferred to tubes containing 3 mL TSB and incubated overnight at 30° C. Bacteria were stored at −80° C. in TSB amended with 20% w/w glycerol.

1.5 Strains Used to Evaluate Antimicrobial Activity

The pathogen strains used as indicators for antimicrobial activity were *E. amylovora* S435 (IRDA, Quebec, Canada), streptomycin-resistant *E. amylovora* S153 (Botany and Plant Pathology, Oregon State University, USA), streptomycin-resistant *E. amylovora* S1605 (MAPAQ, Quebec, Canada).

1.6 First Screening Step: Antagonistic Activity Assays

The antagonistic activities of the bacterial isolates against *E. amylovora* were determined by an agar plate assay.

Method:

Aliquots of bacterial colonies were selected from each bacterial glycerol-frozen stock solution and incubated overnight at 30° C. in 3 mL TSB. Five microliters of each bacterial culture were deposited on lawns of *E. amylovora* 5435 growing on TSA plates. These lawns were first made by incubating 50 μL of *E. amylovora* S435 overnight in 3 mL TSB at 30° C. and then resuspending them in sterile water to get an $OD_{620}$ of 0.2. Finally, 100 μL of the suspensions were spread onto TSA plates. The plates were incubated at room temperature (~21° C.) for 2 d. Bacterial isolates forming clear haloes (inhibition zones; see FIG. 1A) on the *E. amylovora* S435 lawns were selected for the second screening step.

1.7 Second Screening Step: Antimicrobial Activity Assays

For evaluation of the extracellular antimicrobial activity, bacterial isolates produced clear inhibition zones in at least one of the previous assays were inoculated into 3 mL TSB at 30° C. and 150 rpm on a rotary shaker for 2 d. The cultures were then centrifuged at 18,000×g for 10 min at 20° C. and the supernatants were passed through a 0.22-μm pore diameter filter to obtain sterile supernatant.

Antimicrobial activity against *E. amylovora* S435 was assessed using a well-diffusion inhibition assay. First, lawns of the test bacteria were grown on agar plates. Fifty microliters of *E. amylovora* S435 were incubated overnight in 3 mL TSB at 30° C. and 150 rpm and then resuspended in sterile water ($OD_{620}$=0.2). The suspensions were spread onto TSA plates and left to air-dry. Wells were bored into the agar with a sterile glass tube (d=10 mm) and filled with 200 μL cell-free bacterial culture supernatant. The plates were then incubated at room temperature (~21° C.) and the diameters of the inhibition zones around the wells were measured after 2 d. For the control, 200 μL TSB were added to one well. Plates were incubated under the same conditions described in previous sections. Each treatment was performed in triplicate.

1.8 In Vitro Growth and Co-Culture Competition

The growth and competition of the active strains were measured by co-culturing them with *E. amylovora* S435, S153 or S1605 in liquid media. Using TSB cultures incubated overnight, 50 μL of each test bacterium (diluted to $OD_{620}$=0.02) were mixed with 50 μL *E. amylovora* strains ($OD_{620}$=0.02) and cultivated in 3 mL TSB at 30° C. with agitation at 150 rpm for 24 h. Serial dilutions up to $10^{-6}$ were then prepared. One hundred microliters of each co-culture dilution were spread onto TSA plates and incubated at room temperature (~21° C.). After 2-3 d, the colony-forming units (CFUs) were counted (*Erwinia* colonies were always distinct from the test isolates). For the control, 50 μL of pure *E. amylovora* 5435 ($OD_{620}$=0.02) was cultured.

1.9 Identification of Bacterial Isolates

DNA Extraction

DNA of active bacterial isolates were extracted according to Fastprep™ procedures and instruments (MP Biomedicals, Solon, Ohio, USA) The dry DNA pellet was resuspended in 50 μL sterile $ddH_2O$ and maintained at −20° C.

16S rRNA Gene Sequence Analysis

PCR amplification of the gene encoding the 16S rRNA was performed to identify the isolates of interest according to the Table 1A below.

TABLE 1A

Primers used to determine 16S rRNA and specific genes of active bacterial isolates

| Target | Primers | Sequence 5'→3' | Approx. product size (bp) |
|---|---|---|---|
| rpoB gene | rpoB-f | AGGTCAACTAGTTCA GTATGGAC (SEQ ID NO: 1) | 579 |
| | rpoB-r | AAGAACCGTAACCGG CAACTT (SEQ ID NO: 2) | |
| rpoB gene | rpoB1698f | AACATCGGTTTGATC AAC (SEQ ID NO: 3) | |
| | rpoB2041r | CGTTGCATGTTGGTA CCCAT (SEQ ID NO: 4) | |
| gyrA gene | gyrA-f | CAGTCAGGAAATGCG TACGTCCTT (SEQ ID NO: 5) | 1025 |
| | gyrA-r | CAAGGTAATGCTCCA GGCATTGCT (SEQ ID NO: 6) | |
| gyrB gene (amplification) | UP-1 | GAAGTCATCATGACC GTTCTGCAYGCNGGN GGNAARTTYGA (SEQ ID NO: 7) | 1200 |
| | UP-2r | AGCAGGGTACGGATG TGCGAGCCRTCNACR TCNGCRTCNGTCAT (SEQ ID NO: 8) | |
| gyrB gene (sequencing) | UP-1S | GAAGTCATCATGACC GTTCTGCA (SEQ ID NO: 9) | 1200 |
| | UP-2Sr | AGCAGGGTACGGATG TGCGAGCC (SEQ ID NO: 10) | |
| | T7 | TTGTAATACGACTCA CTATAGGG (SEQ ID NO: 11) | |
| 16 sRNA | pA-27f-YM | AGAGTTTGATYMTGG CTCAG (SEQ ID NO: 12) | 1500 |

TABLE 1A-continued

Primers used to determine 16S rRNA and specific genes of active bacterial isolates

| Target | Primers | Sequence 5'→3' | Approx. product size (bp) |
|---|---|---|---|
| | pH | AAGGAGGTGATCCAR CCGCA (SEQ ID NO: 13) | |

PCR was carried out in a 50-μL reaction mixture consisting of 1× Taq buffer, 200 dNTPs mix, 0.4 μM pA-27f-YM, 0.4 μM pH, 1 unit Feldan Taq DNA Polymerase (BioBasic Canada Inc., Markham, Ontario, Canada), and 50 ng extracted DNA. The amplifications were performed in a C1000 Touch™ Thermal Cycler (Bio-Rad Laboratories Ltd., Mississauga, Ontario, Canada) using an initial DNA denaturation step of 5 min at 95° C. followed by 29 cycles of 30 s at 95° C., primer annealing for 40 s at 55° C., primer elongation for 1.5 min at 72° C., and a final extension step for 10 min at 72° C. After DNA amplification, the PCR products were analyzed by agarose gel electrophoresis (1.0% w/v agarose, 100 V, 60 min). The DNA was stained with ethidium bromide (0.5 μg/mL) and visualized under UV illumination.

16S rRNA Gene Sequence Analysis Via Resphera Insight v 2.2

Resphera Insight v. 2.2 (Resphera Biosciences, Baltimore, Md., USA), which provides ultra-high-resolution taxonomic assignment of 16S rRNA sequences down to the species level, was used as illustrated by the manufacturer to predict an accurate consensus lineage of the active isolates.

Amplification of specific *Bacillus* and *Paenibacillus* genes: The rpoB, gyrA, and gyrB gene fragments were used as molecular diagnostic markers to identify isolates within the *Bacillus subtilis* group. To this end, specific primers for the amplification of each gene were used (Table 1A). PCR amplifications were carried out in a 25-4, reaction mixture as described above, using the appropriate forward and reverse primers. The amplifications were performed using specific PCR temperature protocols. After DNA amplification, the rpoB, gyrA, and gyrB fragments were analyzed by agarose gel electrophoresis (Tables 1A and 1B).

TABLE 1B

Temperature program for amplification of DNA fragments of specific genes by PCR

| | Protocol | | | |
|---|---|---|---|---|
| Step | rpoB | gyrA | gyrB | |
| 1 | 5 min @ 95° C. | 5 min @ 95° C. | 5 min @ 95° C. | initial denaturation |
| 2 | 1 min @ 95° C. | 30 s @ 95° C. | 1 min @ 95° C. | denaturation |
| 3 | 1 min @ 51° C. | 45 s @ 51° C. | 1 min @ 60° C. | annealing |
| 4 | 1 min @ 72° C. | 1 min @ 72° C. | 2 min @ 72° C. | elongation |
| 5 | Repeat steps 2-4 | Repeat steps 2-4 | Repeat steps 2-4 | 29× |
| 6 | 10 min @ 72° C. | 10 min @ 72° C. | 10 min @ 72° C. | final elongation |
| 7 | ∞ 4° C. | ∞ 4° C. | ∞ 4° C. | stop PCR reaction and refrigerate DNA products |
| 8 | end | end | end | |

To refine the identification of the *Paenibacillus* spp. isolates, the rpoB gene was amplified (Table 1B). PCR amplifications were carried out in a 25-4, reaction mixture with 1× Taq buffer, 200 μM dNTPs mixture, 0.4 μM of each primer, 1 unit Feldan Taq DNA Polymerase, and 50 ng bacterial DNA. The amplifications were performed as described above except that the primer was elongated for 35 s at 72° C. After DNA amplification, the rpoB fragments (240 bp) were analyzed by agarose gel electrophoresis.

All PCR products were excised and purified from the agarose gel using a gel extraction kit (Bio Basic Canada Inc., Markham, Ontario, Canada) and sequenced at Institut de recherches cliniques de Montreal (IRCM). The same primers were used for the initial PCR reaction and the sequencing reactions with 16S rRNA and the rpoB gene from the *Paenibacillus* sp. isolates. The rpoB fragments from the *Bacillus* sp. isolates were cloned into a pGEM-T-Easy Vector™ (pGEM-t Easy Kit, Promega, Madison, Wis., USA) and sequenced using the universal primers Sp6 and T7. The gyrA fragments were sequenced with the same primers used in the initial PCR. The gyrB fragments were amplified with the universal primers UP-1 and UP-2r and sequenced with the UP-1S and the UP-2Sr primers.

The sequences obtained for each isolate were processed with the BioEdit™ sequence alignment editor (*Ibis* Therapeutics, Carlsbad, Calif., USA) and analyzed with Ribosomal Database Project RDP (https://rdp.cme.msu.edu/segmatch/segmatch_intro.jsp). If the sequence identity was >99%, it was considered that the bacterial isolates belonged to the same species. If the sequence identity was >97%, then the strains were classified in the same genus or family.

1.10 in Planta Testing

Treatment of Apple Leaves and Fruits

For leaf inoculation, *E. amylovora* 5435 was grown for 24 h in 3 mL TSB with shaking at 200 rpm. The culture was diluted with fresh sterile TSB to $OD_{620}$=0.2 which was equivalent to $2\times10^8$ CFU/mL. Silwet L-77 surfactant at a final concentration of 0.025% (v/v) was added to the cell suspension to facilitate penetration of the pathogenic bacteria. McIntosh leaves were collected from apple orchards (IRDA) and stored at 4° C. for 1-5 days prior to treatment. Sterile scissors were soaked in 1 mL *E. amylovora* S435 suspension and used to cut three McIntosh apple leaves replicates per strain in order to inoculate them with *E. amylovora* S435 (one cut of 2-3 cm per leaf). The test strains were grown in 10 mL TSB medium for 2 d at 30° C. and 200 rpm. About 30 min after leaf inoculation, 1 mL per leaf of test strains culture were sprayed with sterile sprayers. They were then stored in Petri dishes unto sterile wet Whatman filter papers and incubated in a growth chamber (25° C., 40% relative humidity (RH), 16-h light/8-h dark photoperiod) for 10 d to determine the efficacy of the isolates against fire blight infection by comparing treated vs. untreated infected leaves which were sprayed with sterile TSB only.

For fruit inoculation, 1 mL *E. amylovora* S435 culture, diluted with fresh sterile TSB to $OD_{620}$=0.2, was injected into McIntosh apples (IRDA orchard) with three fruit replicates per strain using a sterile syringe (one injection 3-5 cm deep per apple). About 30 min after the *Erwinia* inoculation, the test isolates were prepared as described above. One milliliter of each isolate was injected into the same inoculation site on the fruit. The fruits were then incubated in a growth chamber as described above to determine the efficacy of the isolates by comparing treated vs. untreated infected fruit injected with sterile TSB only. The leaves and fruits were evaluated for disease severity by visually rating the percentage of leaf tissue and fruit with lesions 2-10 d after inoculation.

1.11 Biological Control Products Formulation

Six strains were selected from the antagonistic and antimicrobial activity assays based on their ability to control *E. amylovora* in vitro. Each of these products was formulated to suppress the pathogen via the active live strains and the secreted metabolites.

Formulation of Spore-Forming Bacteria

To formulate two products based on strains of *P. polymyxa* 273 and *B. velezensis* (formerly known as *Bacillus amyloliquefaciens*) subsp. *plantarum* FL50S, Schaeffer's sporulation medium (SSM) was used. After incubation for 72 h at 30° C. with agitation at 200 rpm, the cultures were heated for 10 min at 80° C. to kill any vegetative bacteria. These two products, each containing sporulated bacteria and supernatant extracellular metabolites, were prepared in triplicate and stored in polypropylene bottles at room temperature (~21° C.). The effect of heating on the activity of cell-free supernatants (CFS) was evaluated and found to not significantly affect antimicrobial activity.

Formulation of Vegetative Bacteria

For the formulation of products based on vegetative bacteria, *P. poae* FL10F, *P. fluorescens* IRDA4, *P. agglomerans* NY60 and NY130 were cultivated in Difco Nutrient Broth (Becton, Dickinson and Co., Franklin Lanes, N.J., USA) supplemented with 0.5% w/w glycerol to promote the production of secondary metabolites. Each culture was incubated for 2 d at 30° C. with agitation at 200 rpm. Then, NaCl was added at a final concentration of 4% w/w to preserve the bacterial products. Each formulated product, consisting of both vegetative bacteria and their supernatant extracellular metabolites, was prepared in triplicate and stored in polypropylene bottles at room temperature (~21° C.). The same products were formulated as described above but without the addition of NaCl to assess the residual antibacterial action of the isolates (bacteria and metabolites) without preservative.

1.12 Stability and Survival of Stored Isolates In Vivo

Apple leaves (McIntosh) were disinfected by soaking them in 70% v/v ethanol for 1 min. They were then air-dried under a sterile hood for 30 min. Formulation of test bacteria that had been stored at room temperature (~21° C.) for 3 months were diluted at a rate of one part product in twenty parts sterile water. One milliliter of this solution was applied to each leaf with a trigger sprayer. The leaves were incubated on wet filters for 7 d at 25° C. and 40% RH. Three leaves were selected at t=0 and another three were selected after 7 d to count CFUs. Each leaf was cut with sterile scissors, soaked in 5 mL NaCl (0.85% w/v), vortexed for 1 min, and incubated for 30 min with shaking at 200 rpm. Dilution series were prepared and used to inoculate TSA count plates. Three replicates were performed for each treatment described above.

1.13 Management of Fire Blight on Shoots in Apple Trees

A trial was conducted at the IRDA research station in Saint-Bruno-de-Montarville, Québec to evaluate the efficacies of the best isolates previously screened. To simulate fire blight, *Malus* x *domestica* 'McIntosh' cultivar trees were inoculated then treated 2 h later with 20% (w/w) isolate dilutions. Inoculum was obtained by suspending a 5-d culture of the virulent strain *E. amylovora* 5435 in potassium phosphate buffer (pH=6.5) in King B agar which favors the growth of this phytopathogen. The bacterial density was adjusted to $\sim1\times10^9$ CFU/mL. Actively growing potted trees (cv. McIntosh grafted onto M26) were inoculated by transversely bisecting the two youngest leaves with scissors dipped in the inoculum. One or two shoots were inoculated per tree. Two hours after inoculation, candidate biological control agent suspensions were sprayed to runoff onto five trees per treatment using a low-pressure sprayer. The experimental design was completely randomized.

Inoculated controls were sprayed either with water or with the medium used to formulate the candidate biocontrol products. Uninoculated controls were sprayed only with water. The medium applied in Treatment 3 was the same one used to cultivate *P. poae* FL9F, *P. poae* FL10F, *P. agglomerans* NY60, *P. agglomerans* NY130, and *P. fluroescens* IRDA4. It consisted of Nutrient Broth NB supplemented with 0.5% w/w glycerol and a 4% w/w NaCl. The trees were incubated in a growth chamber at 25° C. and observed 2, 4, 7, and 10 d after treatment. Disease severity (DS) was rated as follows: 0=absence of necrosis; 1=necrosis limited to central vein of inoculated leaves; 2=necrosis extending to petiole; 3=necrosis reaching shoot; 4=necrosis reaching other leaves on the inoculated shoot. Fire blight severity scores were reported only 10 d after inoculation. No disease was found on the uninoculated controls. Severity scores were analyzed with a cumulative link mixed model (clmm) in the "ordinal" package of R. Treatment and observation date were used as fixed effects. Individual trees were used as a random effect.

1.14 Field Trial to Control Fireblight on Rome Cultivars in Geneva NY (USA)

A field trial was conducted to determine the performance of the formulated product based on the vegetative cells of *Pseudomonas poae* FL10F and its extracellular metabolites produced in the supernatants and was compared to antibiotic (FireWall 17 WP Streptomycin), copper fungicide (Cueva, Certis, USA) and the biological product Blossom Protect based on two strains of *Aureobasidium pullulans*. The strain (*P. poae* FL10F) was selected because it demonstrated the strongest in vitro antagonistic and antimicrobial activity against *E. amylovora* S435, S153 and S1605. Both antibiotic and copper that were used in this trial were EPA registered products. *Pseudomonas poae* FL10F was cultivated for 2 days at 30° C. and 200 rpm and reached an $OD_{600\ nm}$=2.50, which was empirically determined to represent $2.50\times10^9$ CFU/mL by plating serial dilutions of the suspension and counting colonies. A 4L of product based on *Pseudomonas poae* FL10F and its metabolites was produced as described above and was sprayed more than 2 months later on apple Rome trees. Three samples of this formulated product were retained in sterile 50 mL polypropylene centrifuge tubes at room temperature for long-term activity and bacterial count studies.

The 4L product was used during in a field trial conducted in Phelps, (Geneva) NY to evaluate the product against fire blight. Apple Rome were used for this study that had 5 to 12 blossom clusters per tree. These were 1-year-old trees from Waffler Nursery, Wolcott, N.Y.

The experimental treatments were applied using a $CO_2$ Backpack sprayer that was calibrated to deliver 100 gallons per acre (Trees were sprayed to first drip with a "dilute" solution of products.) The sprayer was calibrated at 42 PSI and used 2 Hollow Cone (TXVK18) Nozzles.

An evaluation of treatments was conducted using the method where scissors were dipped into a solution of a streptomycin sensitive *Erwinia amylovora* strain S01, and the two smallest leaves on each terminal or shoot were cut in half. This severe test is used to simulate infection that can occur following hailstorms. The scissors were dipped into the *Erwinia amylovora* S01 solution prior to each cut. The apical terminal shoot and the terminal leaves on any side shoots were cut. For the size of these trees, the number of terminals that were cut varied from 9 to 18. To evaluate the treatments for this method, each treatment was applied as before to all leaves and shoots of seven individual trees. The inoculations occurred near dusk, and 1.15 inches of rain occurred during the overnight period. All treatments were applied 30 minutes before the infection and then re-applied 24 hours after the initial inoculation. The second application of treatments was applied to the same trees. The product based on Fluorescent *Pseudomonas poae* FL10F and its metabolites was first diluted at a concentration of 20% (w/w) with water then it was mixed properly and sprayed.

At 3 weeks following the scissor inoculation, each terminal shoot was rated for the length in inches with typical symptoms of fire blight (rated as SEVERITY). Then the percentage of all shoots that had any symptoms of fire blight was calculated as INCIDENCE).

Example 2: Isolation of Bacterial Isolates and In Vitro Screening for Anti-*E. amylovora* Activity The leaves, flowers, stems, and fruits of apples, pears, tomatoes, and strawberries, and agricultural field soil samples, were collected from various locations from 2011-2015, as described in Table 2.

TABLE 2

Environmental samples collected from various locations for bacterial isolation

| Sample | Location source and sampling date | Number of samples |
|---|---|---|
| Agricultural field soil | [A]: Apple and pear orchards, Mont-Saint-Bruno (IRDA) Québec, Canada, September 2014 | 4 |
| Agricultural field soil | [B]: Apple and pear orchards, Oka, Québec, Canada, September, 2014 | 3 |
| Agricultural field soil | [C]: Sherrington, Québec, Canada, September, 2014 | 4 |
| Agricultural field soil | [D]: Wimauma, Florida, USA, April, 2013 | 1 |
| Agricultural field soil | [E]: Sherrington, Québec, Canada, November, 2011 | 4 |
| Agricultural field soil | [F]: Wimauma, Florida, USA, July, 2012 | 2 |
| Strawberry leaves | [G]: Dover, Florida, USA, April, 2013 | 1 |
| Tomato leaves and fruits | [H]: Wimauma, Florida, USA, July, 2012 | 3 |
| Apple (McIntosh and Honeycrisp cultivars) and pear (Beauté Flamande cultivar) leaves, stems, and fruits | [I]: Apple and pear orchard, Mont-Saint-Bruno (IRDA), Québec, Canada, September, 2014 | 4 |

TABLE 2-continued

| Environmental samples collected from various locations for bacterial isolation | | |
|---|---|---|
| Sample | Location source and sampling date | Number of samples |
| Tomato leaves and fruits | [J]: Sherrington, Québec, Canada, November, 2011 | 4 |
| Leaves, stems, and fruits of various plants | [K]: Orchard, Laval, Québec, Canada, September, 2014 | 4 |
| Flowers, leaves, stems, and soil of Empire, Marshall McIntosh, Cortland, Mcintosh, Paula Red, Honey crisp, Royal Court and Lobo apple cultivars | [L]: Apple and pear orchards, Mont-Saint- Bruno (IRDA), Québec, Canada, May-September, 2015 | 30 |
| Apple leaves, stems, and soil | [M]: Apple trees, Laval, Québec, Canada, June, 2015 | 5 |
| Rome apple leaves and stems | [N]: Geneva, New York, USA, July, 2015 | 5 |
| Pear flowers, leaves, and stems | [O]: Laval, Québec, Canada, May, 2015 | 5 |
| | Total | 79 |

A total of 79 environmental samples were analyzed. About 5,000 isolates were tested against *E. amylovora* 5435 using a direct antagonistic activity assay as the first screening step. Of all the isolates assayed, 205 strains produced inhibition zones of varying diameters on a lawn of *E. amylovora* S435 (FIG. 1A). These 205 selected isolates were stored at −80° C., and the antagonistic screening process was repeated three times with similar results.

Figure 1B:
FIG. 1B shows antimicrobial activity of two bacterial isolate cell-free supernatants (CFS) against a lawn of *E. amylovora* S435, wherein inhibition zones are indicated by dotted circles. Left: isolate *P. poae* FL3F; Right: isolate *P. poae* FL4F.
Figure 2A:
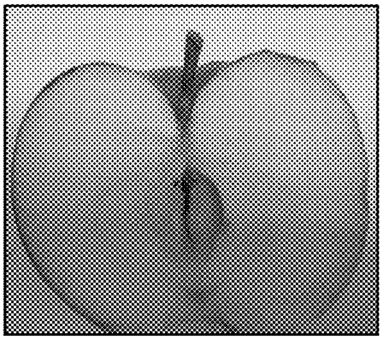
FIGS. 2A-2G show representative images of apples inoculated with *E. amylovora* and treated with various antimicrobial control agents or antibiotics. Apples were cut 10 d after treatment.
Figure 2B:
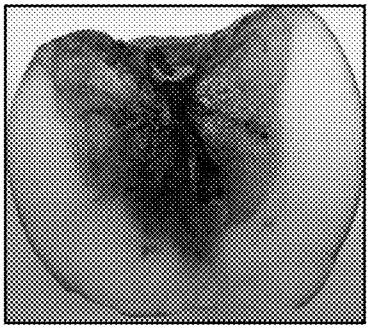
Figure 2C:
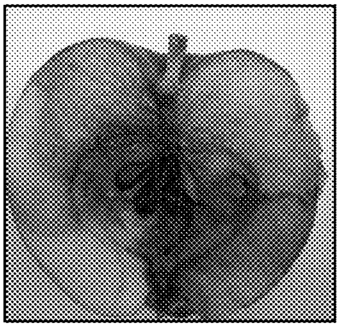
Figure 2D:
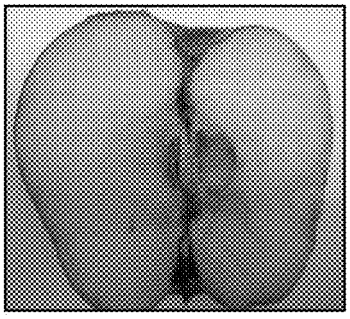
Figure 2E:
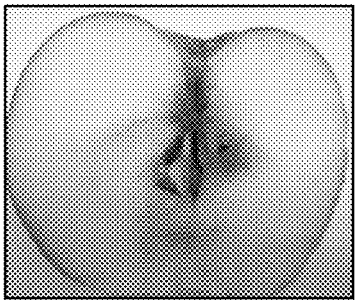
Figure 2F:
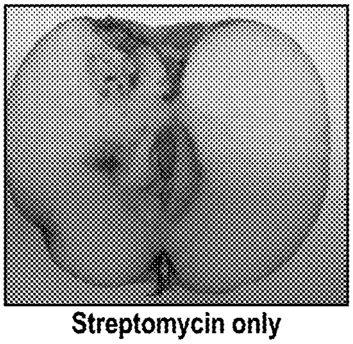
Figure 2G:
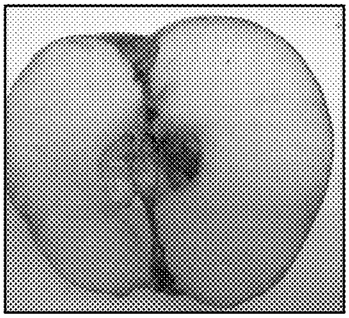
Figure 3A:
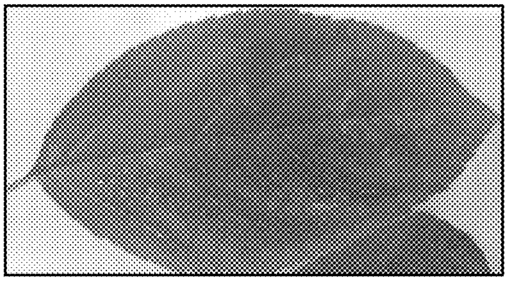
FIGS. 3A-3G show apple leaves cut with scissors inoculated with *E. amylovora* S1605 at $OD_{620}$=0.2 and treated with various antimicrobially active isolates. Observations were made 10 d after inoculation.
Figure 3B:
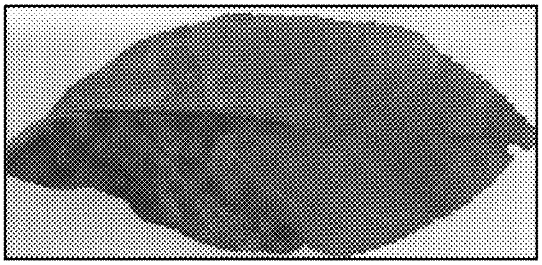
Figure 3C:
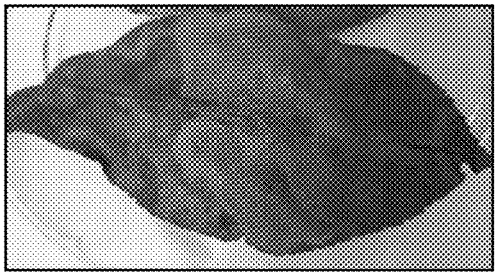
Figure 3D:
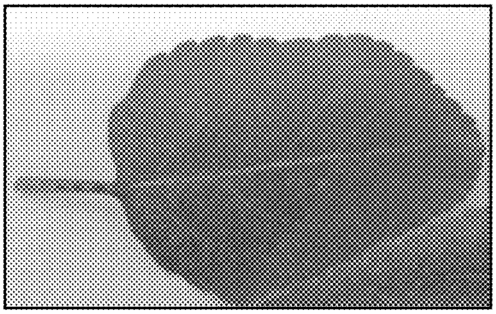
Figure 3E:
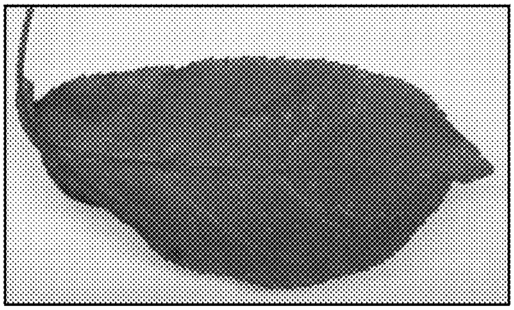
Figure 3F:
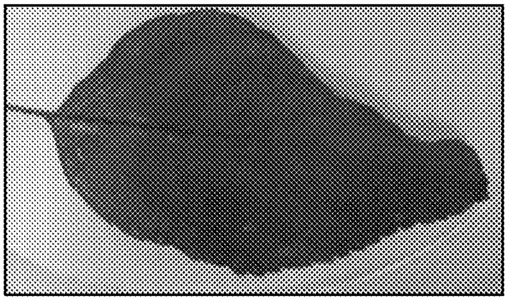
Figure 3G:
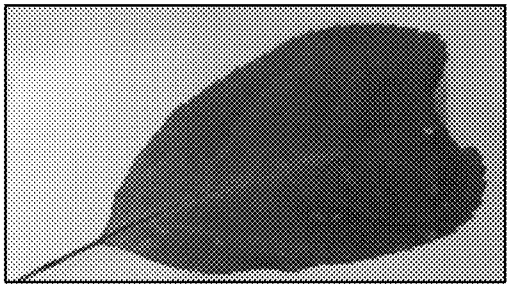

For the second screening step, the extracellular antimicrobial activities of the 205 isolates were determined and 32 isolates were retained for their cell-free supernatants (CFS) activities (FIG. 1B and Table 3). The CFS of *P. polymyxa* 273, *P. poae* FL10F, and *B. velezensis* subsp. *plantarum* FL50S, displayed the strongest activity against *E. amylovora* S435. They also inhibited the growth of streptomycin-resistant *E. amylovora* S153 and *E. amylovora* S1605 (Tables 3 and 4). Cell-free supernatants from these three isolates formed inhibition halos 25.0-35.0 mm in diameter on *E. amylovora* S435 cultures and were subjected to further analyses in Table 4.

TABLE 3

| Activities of CFS against *Erwinia amylovora* S435 | | | | | |
|---|---|---|---|---|---|
| Bacterial isolates/ 16S rRNA gene sequence identification = 99% similarilty | Source | Medium of isolation | Diameter of growth inhibition zone (including well diameter)*, mm | 2-fold diluted CFS | 10-fold diluted CFS |
| *Paenibacillus polymyxa* 273 | [E] | Benedict | 26.66 ± 0.34 | 21.00 ± 0.36 | 17.58 ± 0.50 |
| *Paenibacillus polymyxa* 344 | [J] | TSA | 23.67 ± 0.21 | 17.08 ± 0.27 | no inhibition |
| *Bacillus velezensis* subsp. *plantarum* FL50S | [F] | PCA | 28.58 ± 0.33 | 27.16 ± 0.21 | 19.08 ± 0.27 |
| *Bacillus velezensis* 304 | [E] | Benedict | 27.25 ± 0.30 | 20.16 ± 0.30 | No inhibition |
| *Bacillus* sp. FD308 | [A] | TSA | 27.42 ± 0.41 | 25.16 ± 0.27 | No inhibition |
| *Bacillus* sp. 331 | [J] | TSA | 28.30 ± 0.42 | 20.50 ± 0.43 | No inhibition |
| *Bacillus* sp. FD402 | [B] | TSA | 24.50 ± 0.43 | 20.16 ± 0.47 | No inhibition |
| *Bacillus velezensis* 417 | [E] | TSA | 27.33 ± 0.60 | 20.16 ± 0.60 | No inhibition |
| *Bacillus* sp. 418 | [E] | TSA | 26.75 ± 0.31 | 19.58 ± 0.25 | No inhibition |
| *Bacillus subtilis* 421 | [E] | TSA | 25.16 ± 0.21 | 22.66 ± 0.42 | No inhibition |
| *Bacillus velezensis* 431 | [E] | TSA | 27.16 ± 0.40 | 20.16 ± 0.30 | No inhibition |
| *Bacillus* sp. FD604 | [A] | TSA | 27.41 ± 0.20 | 21.33 ± 0.49 | No inhibition |
| *Bacillus* sp. IRDA27 | [L] | TSA | 25.50 ± 0.34 | 20.16 ± 0.30 | No inhibition |
| *Bacillus* sp. IRDA63 | [L] | TSA | 23.50 ± 0.34 | 17.08 ± 0.27 | No inhibition |
| *Bacillus* sp. IRDA618 | [L] | TSA | 23.50 ± 0.50 | 19.50 ± 0.18 | No inhibition |
| *Bacillus* sp. IRDA619 | [L] | TSA | 21.50 ± 0.50 | 16.50 ± 0.22 | No inhibition |
| *Bacillus* sp. IRDA627 | [L] | TSA | 25.50 ± 0.34 | 20.16 ± 0.30 | No inhibition |
| *Bacillus* sp. IRDA672 | [L] | TSA | 24.00 ± 0.50 | 21.50 ± 0.34 | No inhibition |
| *Bacillus* sp. IRDA675 | [L] | TSA | 23.50 ± 0.50 | 16.50 ± 0.22 | No inhibition |
| *Bacillus* sp. IRDA683 | [L] | TSA | 29.16 ± 0.30 | 25.16 ± 0.27 | No inhibition |
| *Bacillus* sp. IRDA684 | [L] | TSA | 24.00 ± 0.50 | 21.50 ± 0.34 | No inhibition |
| *Bacillus* sp. IRDA685 | [L] | TSA | 25.50 ± 0.34 | 21.00 ± 0.36 | No inhibition |
| *Bacillus* sp. IRDA687 | [L] | TSA | 22.50 ± 0.50 | 17.08 ± 0.27 | No inhibition |
| *Pseudomonas poae* FL3F | [G] | PCA | 28.10 ± 0.27 | 25.16 ± 0.30 | 19.50 ± 0.18 |
| *Pseudomonas poae* FL4F | [G] | PCA | 29.92 ± 0.20 | 23.75 ± 0.31 | 21.50 ± 0.34 |
| *Pseudomonas poae* FL9F | [G] | PCA | 26.00 ± 0.26 | 23.50 ± 0.34 | 16.50 ± 0.22 |
| *Pseudomonas poae* FL10F | [G] | PCA | 35.08 ± 0.27 | 30.41 ± 0.37 | 25.10 ± 0.27 |
| *Pseudomonas fluorescens* IRDA4 | [L] | TSA | 29.16 ± 0.30 | 19.50 ± 0.18 | No inhibition |
| *Pseudomonas* sp. 41 | [L] | TSA | 23.25 ± 0.36 | 20.16 ± 0.30 | No inhibition |
| *Pseudomonas* sp. 42 | [L] | TSA | 23.33 ± 0.35 | 17.08 ± 0.27 | No inhibition |
| *Pseudomonas* sp. 43 | [L] | TSA | 23.50 ± 0.34 | 19.58 ± 0.25 | No inhibition |
| *Pseudomonas* sp. NY1238 | [L] | TSA | 21.17 ± 0.40 | 16.50 ± 0.22 | No inhibition |
| *Pantoea agglomerans* NY50 | [N] | TSA | No activity | No activity | No activity |

TABLE 3-continued

Activities of CFS against *Erwinia amylovora* S435

| Bacterial isolates/ 16S rRNA gene sequence identification = 99% similarilty | Source | Medium of isolation | Diameter of growth inhibition zone (including well diameter)*, mm | 2-fold diluted CFS | 10-fold diluted CFS |
|---|---|---|---|---|---|
| *Pantoea agglomerans* NY60 | [N] | TSA | No activity | No activity | No activity |
| *Pantoea agglomerans* NY130 | [N] | TSA | No activity | No activity | No activity |
| *Pantoea agglomerans* IRDA36 | [L] | TSA | No activity | No activity | No activity |
| *Pantoea agglomerans* IRDA59 | [L] | TSA | No activity | No activity | No activity |

Tryptic Soy Agar (TSA), Plate Count Agar (PCA).
Benedict, ± Standard error of the mean (SEM) of three replicates,
*Well diameter = 10 mm.

TABLE 4

Efficacies of the extracellular metabolites of *P. polymyxa* 273, *B. velezensis* FL50S and *Pseudomonas poae* FL10F against *E. amyloyora* S153 and S1605

| Bacterial isolates | Diameter of growth inhibition zone of *E. amylovora* strains (including well diameter)*, mm S153 | S1605 |
|---|---|---|
| *Paenibacillus polymyxa* 273 | 25.00 ± 0.25 | 25.58 ± 0.37 |
| *Bacillus velezensis* subsp. *plantarum* FL50S | 27.30 ± 0.42 | 27.83 ± 0.40 |
| *Pseudomonas poae* FL10F | 29.58 ± 0.52 | 33.08 ± 0.27 |

± Standard error of the mean (SEM) of three replicates,
*Well diameter = 10 mm.

To increase agar diffusion assay sensitivity and address relative differences in metabolite solubility, CFS of the strains most active against *E. amylovora* (with the largest inhibitory zones, Table 3) were diluted by 2-fold and 10-fold, and the *E. amylovora* S435 inhibition zone assays were repeated. CFS from six of the isolates retained some inhibitory activity even at a 10-fold dilution: *P. polymyxa* 273; *B. velezensis* subsp. *plantarum* FL50S; *P. poae* FL3F; *P. poae* FL4F; *P. poae* FL9F; and *P. poae* FL10F (see Table 3).

Surprisingly, a subgroup of five *P. agglomerans* isolates (NY50, NY60, NY130, IRDA36, IRDA59) selected because of their strong inhibitory activity in direct antagonism assays (see e.g., Table 5), even in comparison to a plurality of other isolates from the same species eliminated following the first screenings, produced CFS with no visible inhibitory activity against *E. amylovora* S435 (see Table 3).

TABLE 5

Direct antagonistic activity of *Pantoea* isolates against *E. amylovora* S435

| Bacterial isolates | *Pantoea* colony diameter (mm)/inhibition zone on *E. amylovora* S435 lawn (including *Pantoea* diameter in mm) |
|---|---|
| *P. agglomerans* NY50 | 11.33 ± 0.33/28.33 ± 0.33 |
| *P. agglomerans* NY60 | 10.00 ± 0.57/30.66 ± 0.33 |
| *P. agglomerans* NY130 | 10.66 ± 0.66/31.33 ± 0.66 |
| *P. agglomerans* IRDA36 | 10.66 ± 0.66/25.33 ± 0.66 |
| *P. agglomerans* IRDA59 | 10.33 ± 0.66/26.33 ± 0.88 |

All strains were isolated on TSA plates.
±Standard error of the mean (SEM) of three replicates

Example 3: In Planta Testing of Apples and Leaves Inoculated with *E. amylovora*

Two in planta experiments were then performed: (1) infections of apples by *E. amylovora* and subsequent injection of an active strain, and (2) infection of apple leaves by *E. amylovora* via scissor-cutting and subsequent spraying of active strains, to assess their biocontrol potential. The 37 active strains were tested in these in planta experiments.

Strikingly, some *P. agglomerans* strains (e.g., NY60) showed comparable efficacy to the streptomycin antibiotics, controlling around 80% disease severity in apples and around 40% in leaves as shown in FIGS. 2 and 3. No phytotoxicity was observed with the *P. agglomerans* NY60 treatment. Disease symptoms on the leaves were observed and recorded independently by two separate technicians. Disease severity and incidence assessments were made based on the results compiled from three separate experiments.

Example 4: Identification of Active Isolates 4.1 16S rRNA

A 1.6-kb 16S rRNA DNA fragment was amplified and sequenced for each bacterial isolate. Thirty-seven bacterial isolates were identified by gene sequencing (Table 3), including 21 isolates belonging to the *Bacillus subtilis* group and 2 isolates belonging to the *Paenibacillus* genus. Analysis of pairwise 16S rDNA sequence alignments were highly similar to each other at the genus level, but could not be used to distinguish different but closely related bacterial species such as *P. polymyxa, P. peoriae, P. jamilae*, and *P. kribbensis*. Nine isolates belonging to the fluorescent *Pseudomonas* group and five isolates belonging to the *Pantoea agglomerans* species were also identified.

4.2 Further Identification of *Pseudomonas* and *Pantoea* Strains Using Resphera Insight™ (v2.2)

Resphera Insight™ (v2.2) which is a clinical-grade proprietary analysis protocol developed to provide ultra-high-resolution taxonomic assignment of 16S rRNA sequences to species-level membership was used to further identify *Pseudomans* and *Pantoea* strains. This computationally intensive procedure maintains the capacity for 99.9% sensitivity and >99.5% species-level specificity for hundreds of bacterial strains, and in cases of ambiguous membership, predicts an accurate consensus lineage. The results Resphera Insight™ (v2.2) were supportive to the 16S rRNA findings (Tables 6 and 7).

TABLE 6

Summary of further *Pseudomonas* strains identification for isolates FL10F, FL9F, FL3F and IRDA4

| Isolates | FL10F CFSAN034337 | FL9F CFSAN055119 | FL3F CFSAN 034336 | IRDA4 CFSAN055120 |
|---|---|---|---|---|
| | Isolates identification (% similarity) | | | |
| Resphera Insight | *Pseudomonas poae* 99% | *Pseudomonas poae* 99% | *Pseudomonas poae* 98% | Fluorescent *Pseudomonas* spp. 99% |

TABLE 7

Summary of further *Pantoea* strains identification for isolates NY60 and NY130

| Isolates | NY60 CFSAN047153 | NY130 CFSAN047154 |
|---|---|---|
| | Isolates identification (% similarity) | |
| Resphera Insight | *Pantoea agglomerans* 99% | *Pantoea agglomerans* 99% |

4.3 Identification of Isolates Via gyrA, gyrB and rpoB Gene Sequences

The gyrA and gyrB sequences were used to discriminate the isolates belonging to the *Bacillus subtilis* group. Isolate 50S most closely resembled *Bacillus velezensis*; their sequence similarity was 99%. Partial sequencing of the gene encoding the B protein subunit of DNA gyrase (gyrB) was performed on the FL3F, FL4F, FL9F, and FL10F isolates, all of which most nearly resemble a *Pseudomonas fluorescens* group strain with sequence similarities of 99-100%. Based on the rpoB gene sequence, isolate 273 was 99% similar to a *P. polymyxa* strain.

4.4 Whole-Genome Sequencing

Genomic DNA was isolated from an overnight culture of each strain using a QiagenDNeasy™ blood and tissue kit (Qiagen Inc., Valencia, Calif.). Genome sequencing was performed using Illumina MiSeg™ sequencing system (Illumina, San Diego, Calif.), achieving >50× average genome coverage. De novo assembly was created for each genome using SPAdes 3.0.0 (St. Petersburg genome assembler) and annotated with the NCBI Prokaryotic Genomes Automatic Annotation Pipeline (http://www.ncbi.nlm.nih.gov/genomes/static/Pipeline.html). Taxonomy of each isolate was assigned using Kraken.

The two-way ANI calculator (http://enve-omics.ce.gatech.edu/ani/index) was used to estimate the average nucleotide identity between genomic datasets of the best anti-*Erwinia* bacterial isolates and already known type strains of *Pantoea, Pseudomonas, Paenibacillus* and *Bacillus* species from NCBI database (http://www.ncbi.nlm.nih.gov/nuccore). If the ANI value between two genomes is above 95%, it means that two isolates belong to the same species.

4.5 Complete Genome Sequencing

Genome mining of biosynthetic gene clusters including non-ribosomal peptide synthetases (NRPSs) and other secondary metabolites were predicted with antibiotics & Secondary Metabolite Analysis SHell (antiSMASH) web server (http://antismash.secondarymetabolites.org/).

For the strain 273, the genome coverage was as high as 88% (N50=364,236 bp) and the resulting number of contigs was calculated to be 206. Only 7.37% of the reads were unclassified which reflect the accuracy of the species identification. The confidence score and species check percentage was as high as 90.91% indicating that the strain 273 is indeed a *Paenibacillus polymyxa* species.

Concerning the strain FL50S, the genome coverage was as high as 78% (N50=132,866 bp) and the resulting number of contigs was calculated to be 105. Only 5.20% of the reads were unclassified which reflect the accuracy of the species identification. The confidence score and species check percentage was as high as 93.26% indicating that the strain FL50S is indeed a *Bacillus velezensis* species with a percentage of 11.63 for the subsp. *Plantarum*. The gene clusters for non-ribosomal peptide synthetases (NRPSs) and other secondary metabolites for isolates 50S, 273, FL3F, FL9F, FL10F, IRDA4, NY60 and NY130, are illustrated in Tables 7A-7C. Strikingly, although the NY60 and NY130 strains were isolated from independent environmental samples, their genomic sequences—particularly with respect to non-ribosomal peptide synthetases and other secondary metabolites—were extremely similar suggesting that such genomic sequences may be used to identify these strains, as well as other *P. agglomerans* strains of having potent anti-*Erwinia* activity.

TABLE 7A

Summary of the complete genome sequencing and major gene clusters for non-ribosomal peptide synthetases (NRPSs) and secondary metabolites for isolates 50S and 273

| Isolate | 50S CFSAN034340 LYNC00000000: accession numbers NCBI assigned after annotation Annotated as '*Bacillus velezensis*' | 273 CFSAN034343 LYND00000000: accession numbers NCBI assigned after annotation |
|---|---|---|
| | Genome sequencing and species check | |
| Genome coverage | 78% | 88% |
| N50 (bp) | 132.866 | 364.236 |
| Number of contigs | 105 | 206 |
| Unclassified reads | 5.20% | 7.37% |
| Confidence score and species check | 93.26% for *Bacillus velezensis* | 90.91% for *Paenibacillus polymyxa* |
| Subsp. | 11.63% for *Plantarum* | – |

TABLE 7A-continued

Summary of the complete genome sequencing and major gene clusters for non-ribosomal peptide synthetases (NRPSs) and secondary metabolites for isolates 50S and 273

| Isolate | 50S CFSAN034340 LYNC00000000: accession numbers NCBI assigned after annotation Annotated as '*Bacillus velezensis*' | 273 CFSAN034343 LYND00000000: accession numbers NCBI assigned after annotation |
|---|---|---|
| Biosynthetic gene clusters % similarity for non-ribosomal peptide synthetases (NRPSs) and other secondary metabolites | | |
| Macrolactin | 100% | – |
| Bacillaene | 85% | 28% |
| Difficidin | 53% | – |
| Iturin | 22% | – |
| Bacilysin | 100% | – |
| Surfactin | 47% | – |
| Bacteriocin | – | – |
| Bacillibactin | 92% | – |
| Kalimantacin/batumin | – | – |
| Fengycin | 80% | – |
| Nosperin | – | 46% |
| Bacillomycin | – | – |
| Fusaricidin | – | 100% |
| Paenibacterin | – | 60% |
| Polymyxin | – | 100% |
| Bacitracin | – | 22% |
| Tridecaptin | – | 80% |
| Plipastatin | 23% | – |
| Teichuronic acid | 100% | – |
| Subtilin | – | – |
| Locillomycin | 28% | – |
| Myxovirescin | – | 8% |
| Citrulline | 27% | – |
| Bacitracin | – | – |
| Paenibacillin | – | – |

TABLE 7B

Summary of the complete genome sequencing and major gene clusters for non-ribosomal peptide synthetases (NRPSs) and secondary metabolites for isolates FL10F, FL9F, FL3F and IRDA4

| Isolates | FL10F CFSAN034337 | FL9F CFSAN055119 | FL3F CFSAN034336 | IRDA4 CFSAN055120 |
|---|---|---|---|---|
| Isolates identification (% similarity) | | | | |
| 16S ribosomal RNA Resphera Insight | *Pseudomonas poae* 99% | *Pseudomonas poae* 99% | *Pseudomonas poae* 98% | Fluorescent *Pseudomonas* spp. 99% |
| Complete genome sequencing - Biosynthetic gene clusters % similarity for non-ribosomal peptide synthetases (NRPSs) and other secondary metabolites | | | | |
| Bacteriocin | + | + | + | + |
| Arylpolyene | 45% | 15% | 45% | 20% |
| Safracin | 90% | 70% | 90% | 90% |
| Pyoverdine | 11% | 3% | 11% | 10% |
| Mangotoxin | 57% | – | 57% | 57% |
| Poaeamide | 100% | – | 100% | 100% |
| Pyochelin | 100% | – | 80% | 80% |
| Tolaasin | – | 50% | – | – |
| Syringafactin | – | – | – | 83% |

+: gene cluster is present on the genome, but the percentage similarity is not determined.

TABLE 7C

Summary of the complete genome sequencing and major gene clusters for non-ribosomal peptide synthetases (NRPSs) and secondary metabolites for isolates NY60 and NY130.

| Isolates | NY60 CFSAN047153 | NY130 CFSAN047154 |
|---|---|---|
| Isolates identification (% similarity) | | |
| 16S ribosomal RNA | *Pantoea agglomerans* | *Pantoea agglomerans* |
| Resphera Insight | 99% | 99% |
| Complete genome sequencing - Biosynthetic gene clusters similarity for non-ribosomal peptide synthetases (NRPSs) and other secondary metabolites | | |
| Bacteriocin | + | + |
| Arylpolyene | 73% | 73% |
| Acyl homoserine lactone (Hserlactone) | + | + |
| Turnerbactin | 30% | 30% |
| Carotenoid | 100% | 100% |
| Desferrioxamine B | 40% | 60% |
| Pyocyanine | 28% | 28% |
| Microcin | + | + |

+: gene cluster is present on the genome, but the percentage similarity is not determined.

Example 5: In Vitro Competition in Co-Cultures

The in vitro competition was assessed by co-culturing active strains (i.e., those characterized in Tables 7A-7C) with *E. amylovora* S435, S153, and S1605 strains. Not all active strains completely killed all colonies of *E. amylovora* strains. Interestingly, only *Pantoea agglomerans* NY60 and NY130 completely killed *E. amylovora* strains S435, S153, and S1605 when they were co-cultivated together.

Example 6: Formulations of Products: Stability and Activity

The objective of this work was to formulate biological control products effective against fire blight on apple and pear trees. Based on the above data, six strains were selected based on their potent activity against *E. amylovora* for the development of formulations. Each of these products was formulated to have a dual mode of action via (1) live strains, and (2) metabolites present in extracellular CFS. Without being bound by theory, when the product is sprayed on the trees, the active metabolites are intended to control *E. amylovora*, while the live bacteria in the formulation are intended to grow, colonize, and outcompete any remaining or forthcoming *E. amylovora*.

The long-term survival of bacteria, and stability of the antagonistic activities of the six biological control formulations were assessed over a period of 9 months. The products were stored at room temperature (~21° C.) in plastic bottles and were found to be relatively stable during the period. Based on CFU/mL counts, the densities of both fluorescent *Pseudomonas* spp. strains and both *Pantoea* strains decreased by ~2 log, and those of those of *P. polymyxa* 273 and *B. velezensis* FL50S by ~1 log, (see Table 8, which presents the means of three replicates).

TABLE 8

Stability of the biological control product formulations

| Biological control product | Concentration of bacteria(CFU/mL) Time: Zero | 3 months | 9 months |
|---|---|---|---|
| *Paenibacillus polymyxa* 273 | $1.10 \pm 0.02 \times 10^7$ | $1.01 \pm 0.01 \times 10^7$ | $2.00 \pm 0.11 \times 10^6$ |
| *Bacillus velezensis* subsp. *Plantarum* FL50S | $2.10 \pm 0.10 \times 10^7$ | $2.00 \pm 0.10 \times 10^7$ | $1.03 \pm 0.06 \times 10^7$ |
| *Pseudomonas poae* FL10F | $1.06 \pm 0.08 \times 10^9$ | $1.96 \pm 0.14 \times 10^8$ | $1.96 \pm 0.12 \times 10^7$ |
| *Pantoea agglomerans* NY60 | $2.63 \pm 0.06 \times 10^9$ | $1.93 \pm 0.06 \times 10^9$ | $1.00 \pm 0.10 \times 10^7$ |
| *Pantoea agglomerans* NY130 | $2.56 \pm 0.03 \times 10^9$ | $1.96 \pm 0.03 \times 10^9$ | $0.96 \pm 0.13 \times 10^7$ |
| *Pseudomonas fluorescens* IRDA4 | $2.00 \pm 0.10 \times 10^9$ | $1.96 \pm 0.03 \times 10^9$ | $1.96 \pm 0.12 \times 10^7$ |

±Standard error of the mean (SEM) of three replicates

Furthermore, the inhibitory activity of the various CFS (Table 9) and the direct cell-to-cell antagonism (Table 10) of bacteria in the formulations remained active after >9 months storage at room temperature. Heating during the formulation of spore-forming bacteria-based products had no effect on the activity of CFS (Table 9).

TABLE 9

Antimicrobial activity of CFS of the biological control product formulations

| Biological control product | Diameter of growth inhibition zone (including well diameter) *, mm | | |
|---|---|---|---|
| | Time Zero | 3 months | 9 months |
| *Paenibacillus polymyxa* 273 | 26.66 ± 0.34 | 23.33 ± 0.35 | 21.67 ± 0.21 |
| *Bacillus velezensis* subsp. *Plantarum* FL50S | 28.58 ± 0.33 | 26.67 ± 0.16 | 23.50 ± 0.34 |
| *Pseudomonas poae* FL10F | 35.08 ± 0.27 | 33.00 ± 0.50 | 29.16 ± 0.30 |
| *Pseudomonas fluorescens* IRDA4 | 29.16 ± 0.30 | 27.66 ± 0.42 | 23.25 ± 0.36 |

±Standard error of the mean (SEM) of three replicates,
* Well diameter = 10 mm.
*Pantoea* strains were not tested for lack of CFS activity.

TABLE 10

Antagonistic activity of the biological control product formulations

| Biological control product | Time Zero* | 3 months* | 9 months* |
|---|---|---|---|
| *Paenibacillus polymyxa* 273 | 10.00 ± 0.57/ 24.66 ± 0.33 | 11.00 ± 0.00/ 22.66 ± 0.33 | 11.33 ± 0.66/ 22.00 ± 0.00 |
| *Bacillus velezensis* subsp. *Plantarum* FL50S | 11.00 ± 0.57/ 26.00 ± 0.00 | 11.00 ± 0.57/ 26.66 ± 0.33 | 11.00 ± 0.00/ 24.30 ± 0.33 |
| *Pseudomonas poae* FL10F | 10.66 ± 0.33/ 29.66 ± 0.88 | 9.00 ± 0.00/ 28.33 ± 0.66 | 11.00 ± 0.57/ 28.00 ± 0.57 |
| *Pseudomonas fluorescens* IRDA4 | 11.00 ± 0.57/ 29.66 ± 0.33 | 10.00 ± 0.00/ 28.30 ± 0.66 | 9.00 ± 0.00/ 26.00 ± 0.57 |
| *Pantoea agglomerans* NY60 | 10.00 ± 0.57/ 30.66 ± 0.33 | 10.66 ± 0.33/ 29.50 ± 0.28 | 10.00 ± 0.57/ 29.30 ± 0.16 |
| *Pantoea agglomerans* NY130 | 10.66 ± 0.16/ 32.33 ± 0.15 | 10.00 ± 0.57/ 30.66 ± 0.33 | 10.00 ± 0.57/ 28.50 ± 0.28 |

*Biological control product colony diameter (mm)/inhibition zone on *E. amylovora* S435 lawn (mm).
±Standard error of the mean (SEM) of three replicates Survival of formulated bacteria sprayed on apple leaves (McIntosh) was then assessed. Table 11 describes the mean of the three replicates which were performed for each treatment, showing that formulated products remained viable on apples leaves for 7 d.

TABLE 11

Survival of the biological control product formulations on leaves

| Microbial-based products | Time Zero *CFU per leaf | After 7 days *CFU per leaf |
|---|---|---|
| *Paenibacillus polymyxa* 273 | $1.25 \pm 0.006 \times 10^3$ | $1.53 \pm 0.033 \times 10^3$ |
| *Bacillus velezensis* subsp. *Plantarum* FL50S | $1.90 \pm 0.057 \times 10^4$ | $1.76 \pm 0.003 \times 10^4$ |
| *Pseudomonas poae* FL10F | $1.20 \pm 0.088 \times 10^5$ | $1.04 \pm 0.000 \times 10^5$ |
| *Pseudomonas fluorescens* IRDA4 | $1.35 \pm 0.005 \times 10^5$ | $1.35 \pm 0.005 \times 10^5$ |
| *Pantoea agglomerans* NY60 | $2.03 \pm 0.066 \times 10^4$ | $2.20 \pm 0.000 \times 10^4$ |
| *Pantoea agglomerans* NY130 | $1.95 \pm 0.009 \times 10^4$ | $2.00 \pm 0.000 \times 10^4$ |
| Leaves (disinfected with ethanol) | 0.00 ± 0.000 | 0.00 ± 0.000 |

±Standard error of the mean (SEM) of three replicates

Example 7: Field Trial for the Management of Fire Blight on *Malus* x *Domestica 'McIntosh' Apple Cultivar Tree Shoots*

A trial was conducted at the IRDA research station in Saint-Bruno-de-Montarville (Québec) to evaluate the effectiveness of selected active strains against shoot blight. One or two shoots were inoculated with *E. amylovora* per tree. Two hours after inoculation, various active strain preparations were applied to the shoots until runoff using a low-pressure atomizer. Five trees were used per treatment, and the experimental design was completely randomized. Formulations based on *P. polymyxa* 273 and *B. velezensis* 50S were prepared as described herein in Example 1.11 ("Formulation of spore-forming bacteria". Those based on *P. poae* FL9F, *P. poae* FL10F, *P. fluorescens* IRDA4, *P. agglomerans* NY60, and *P. agglomerans* NY130 were formulated as described in "Formulation of vegetative bacteria". They were diluted to 20% (v/v) before application. Trees treated with *P. agglomerans* strains NY60 and NY130 had much less fire blight than the control after 10 days, with Disease Scores (DS) not significantly different from those treated with streptomycin. Fire blight never extended beyond the central vein of the inoculated leaf in trees receiving *P. agglomerans* NY60. No evidence of phytotoxicity appeared in either treatment (Table 12).

TABLE 12

Effects of various treatments on McIntosh apple trees experimentally inoculated with *E. amylovora* S435

| Treatment | Median score | Score range | Tukey** |
|---|---|---|---|
| Streptomycin (100 ppm) | 0 | [0, 2] | a |
| Water | 3.5 | [2, 4] | c |
| Sterile culture medium | 3 | [2, 4] | c |
| *P. polymyxa* 273 | 3 | [1, 4] | bc |
| *P. poae* FL10F | 2 | [1, 3] | bc |
| *B. velezensis* FL50S | 3.75 | [3, 4] | c |
| *P. fluorescens* IRDA4 | 3 | [2, 4] | c |
| *P. agglomerans* NY130 | 1 | [0, 3] | ab |
| *P. agglomerans* NY60 | 1 | [0, 1] | ab |

**Values followed by the same letter are not significantly different (P ≤ 0.05) according to lsmeans (Lenth, 2016) with an adjustment for Tukey's HSD to control for family-wise error.

Example 8: Apple Trees Trial to Control Fire Blight on Rome Cultivars in Geneva NY (USA)

A field trial was conducted to determine the performance of the formulated product based on the living cells of *Pseudomonas poae* FL10F (see Example 1.14). This strain was selected to conduct the trial because of its both: 1) strong cell-free supernatant and 2) antagonistic activity against *E. amylovora* strains.

The objective of this trial was to compare the activity of *P. poae* FL with antibiotic (Streptomycin), copper fungicide (Cueva, Certis, USA) and the biological product Blossom Protect based on two strains of *Aureobasidium pullulans* (Porter et al., 1960). Apple trees were infected with 1×10' CFU/mL solution of *Erwinia amylovora*. The concentration of various treatments applied are represented in Table 13. The medium used in Treatment 7 is the same one used to cultivate the *P. poae* FL composed of Nutrient Broth NB (Difco) supplemented with 0.5% (w/w) glycerol and a concentration of 4% NaCl (w/w). Neither the medium nor the treatments used were phytotoxic to apple leaves and no phytotoxicity was noted on the apple trees in this study.

TABLE 13

Performance of the *P. poae* FL10F product compared to antibiotic and copper products

| Trt No. | Treatment Name | Rate | Rate Unit | Fire blight Severity Average length of shoot with symptoms of Fire blight (INCHES) 1 | | Fire blight Incidence Average percentage of shoots with symptons of Fire blight following inoculation % 2 | | Phytotoxicity Percentage of leaves with atypical symptoms % 3 | |
|---|---|---|---|---|---|---|---|---|---|
| 1 | Untreated | | | 6.12 | a | 82.78 | a | 0.00 | a |
| 2 | Strepmycin | 8 | oz wt/a | 3.89 | bc | 52.39 | bc | 0.00 | a |
| 3 | Strepmycin | 2.4 | oz wt/a | 5.53 | ab | 81.73 | a | 0.00 | a |
| 4 | Medium | 20 | % v/v | 6.13 | a | 82.80 | a | 0.00 | a |
| 5 | Cueva | 64 | fl oz/a | 3.90 | bc | 71.14 | ab | 0.00 | a |
| 6 | *P. poae* FL10F | 20 | % v/v | 2.49 | c | 47.70 | c | 0.00 | a |
| 7 | Blossom Protect | 20 | oz wt/a | 3.25 | c | 52.95 | bc | 0.00 | a |
| | LSD (P = .05) | | | 1.403 | | 12.909 | | 0.000 | |
| | Standard Deviation | | | 1.312 | | 12.075 | | 0.000 | |

Means followed by same letter do not significantly differ (P = .05, Student-Newman-Keuls)

The above severe test was conducted in the field to determine if the product based on *Pseudomonas poae* FL10F and its metabolites can control trauma blight which refers to fire blight infection caused when major weather events (i.e., late frost accompanied by hail or high winds) causing injury to the plant tissue. Each treatment was performed on 7 different trees and each tree was 7 feet tall. More than 82% of all cuts with scissors had infection indicating that the infection of the trees was successful. The above results (Table 13) demonstrated that the *P. poae* FL10F product was even more efficacious than antibiotics and copper products.

Example 9: Identification of Active Metabolites in *B. Velezensis* FL50S, *P. poae* FL10F, and *P. agglomerans* NY60

9.1 Materials and Methods

Bacterial Strains and Growth Conditions

The bacterial strains used in this example are as follows: *B. velezensis* strain FL50S was isolated from an agricultural field soil in Wimauma, Fla., USA, *P. poae* FL10F was isolated from strawberry leaves in Dover, Fla., USA, *P. agglomerans* NY60 was isolated from Rome apple leaves in Geneva, N.Y., USA, and *E. amylovora* 5435 was supplied by IRDA, Quebec, Canada). Unless otherwise specified, the bacteria were routinely grown from frozen glycerol stock by culturing in 3 ml tryptic soy broth (TSB) (BD, New Jersey, USA) overnight in test tubes incubated at 30° C. and shaking in a TC-7 roller drum (New Brunswick Scientific Co., New Brunswick, N.J.) at 240 rpm. For inoculation, the appropriate aliquots of each overnight culture were used to inoculate culture media by adjusting the optical density at 600 nm ($OD_{600}$) to 0.01, corresponding to almost $8\times10^6$ CFU/ml.

Production of Secondary Metabolites Produced by *Bacillus* and *Pseudomonas* Isolates The production of metabolites by bacterial isolates was carried out in 2L conical flasks with 500 ml of respective medium. *P. agglomerans* NY60 was cultivated in Difco Nutrient Broth (Becton, Dickinson and Co., Franklin Lanes, N.J., USA) and was incubated for 2 d at 30° C. with agitation at 200 rpm. King's B medium was used as a production medium for *P. poae* FL10F isolate, while Landy medium was used for cultivation of *B. velezensis* FL50S. Cultures were shaken at 30° C. for 48 h at 250 rpm. Landy medium contains: glucose 20 g/L, L-glutamic acid 5.0 g/L, yeast extract 1.0 g/L, $K_2HPO_4$ 1.0 g/L, $MgSO_4$ ($7H_2O$) 0.5 g/L, KCl 0.5 g/L, $CuSO_4$ 1.6 mg/L, $Fe_2(SO_4)_3$ 1.2 mg/L, $MnSO_4$ 0.4 mg/L.

To obtain cell-free supernatants, cultures of both strains were centrifuged at 25 000 rpm for 1 hour. The pellets were discarded and the supernatants were filtered using Stericup™ vacuum filtration system (0.2 μm). Fresh cell-free supernatants were used for the present research, but they could also be stored at +4° C. for one week, or at −20° C. for 6 months, while keeping their activity.

Secondary Metabolite Gene Cluster Prediction and Analysis

Genome mining of biosynthetic gene clusters including non-ribosomal peptide synthetases (NRPSs), polyketide synthases (PKSs), hybrid PKS/NRPS, siderophores, and bacteriocins were predicted with antibiotics & Secondary Metabolite Analysis SHell (anti SMASH) web server version 5 (http://antismash.secondarymetabolites.org/).

Whole-Genome Sequencing

Genomic DNA was isolated from an overnight culture of each strain using a QiagenDNeasy™ blood and tissue kit (Qiagen Inc., Valencia, Calif.). Genome sequencing was performed using Illumina MiSeg™ sequencing system (Illumina, San Diego, Calif.), achieving >50× average genome coverage. De novo assembly was created for each genome using SPAdes 3.0.0 (St. Petersburg genome assembler), and annotated with the NCBI Prokaryotic Genomes Automatic Annotation Pipeline (http://www.ncbi.nlm.nih.gov/genomes/static/Pipeline.html). Taxonomy of each isolate was assigned using Kraken.

Bioassay-Guided Fractionation and Isolation of Active Metabolites

1 L of each bacterial culture was combined, and biomass was removed by centrifugation at 17 700×g for 20 min. The cell-free medium supernatant was applied to 40 g of pre-equilibrated Amberlite™ XAD-16 resin packed in a column. The XAD-16 column was subsequently washed with 1 L of $H_2O$, and then eluted with 1 L of 100% methanol. The methanolic elution was evaporated to dryness by rotary evaporation, and the brown residue was redissolved in 5 ml of purified water (Milli-Q system; Millipore, Bedford, Mass.). The concentrated solution was then applied onto a 12 gram Biotage® SNAP Ultra C18 column to be fractionate using reverse-phase flash chromatography on a Biotage (Stockholm, Sweden) Isorela One instrument. This chromatography was performed using a linear gradient acetonitrile from 5% to 100% over 50 min at 15 ml $min^{-1}$. To identify column fractions containing active compound, each fraction was evaporated to dryness by rotary evaporation and was redissolved in 2 ml of milliQ™ water. The bioactivity of these fractions was further determined by performing agar disc diffusion assay.

Activity of Cell-Free Supernatants and Fractions Against *Erwinia* Amylovora 5435

In order to estimate the activity of bacterial metabolites and fractions against *E. amylovora* S435, agar disc diffusion assay was performed. Paper blank discs (d=6 mm) were saturated by cell-free supernatants or fractions (20 μl), air dried overnight in the biological cabinet at room temperature (22° C.) for 30 min. The antimicrobial activity was then tested by placing saturated disc on a lawn of *E. amylovora* S435 TSB agar plate and measuring the inhibition area ($mm^2$) of pathogen. This assay was performed in triplicate.

LC-ESI-MS/MS Analysis

The cell-free supernatants and active fractions were further analyzed by high-performance liquid chromatography (HPLC; Waters 2795, Mississauga, ON, Canada) equipped with a 250×4.6 mm i.d. Luna Omega Polar C18 reversed-phase column (particle size 3 μm) using a 1% acetic acid—acetonitrile gradient at a flow rate of 500 μl/min. The detector was a quadrupole mass spectrometer (Quattro Premier XE, Waters). Analyses were carried out in the positive electrospray ionization (ESI) mode with a mass window ranging from m/z 130-1930. Collision-induced dissociation (CID) MS/MS experiments were performed using argon gas at various collision energies.

PacBio® Sequencing and Assembly

Single-molecule, real-time sequencing offers longer read lengths making it well-suited for unsolved problems in genome, transcriptome, and epigenetics research. The highly-contiguous sequencing can close gaps in current reference assemblies and characterize structural variation (SV) in genomes.

The resulting assembled sequences were polished with Illumina reads using a combination of BWA version 0.7.17-r1188, SAMtools version 1.9 and Pilon version 1.22. SAMtools version 1.9 and Pilon version 1.22. The sequences of strain *P. agglomerans* NY60 have been deposited in GenBank under the accession number CP034469.

The sequences of strain *P. agglomerans* NY60 were annotated using the DFAST web server and the eggnog-mapper web server. The genes involved in a type VI secretion system (T6SS) were subsequently investigated with Artemis version 17.0.0 and the BLAST suite following the nomenclature of a study describing this system in *Pantoea ananatis*. Finally, a graphical representation of the T6SS loci was made with EasyFig version 2.2.2.

Random Transposon Mutagenesis and Colony Selection

Transposon insertions in *P. agglomerans* NY60 chromosome were generated by mating *P. agglomerans* NY60 with DAP-dependent *E. coli* strain x7213 carrying pUT/mini-Tn5 Sm/Sp on Lysogeny broth (LB) agar supplemented with DAP at 37° C. Mutagenized cells were plated on TSA plates containing spectinomycin (15 μg/ml). The plates were incubated at room temperature (~21° C.) for 2 d. Thereafter, a lawn of streptomycin-resistant *E. amylovora* S435 were spread onto TSA plates. After incubation for another 2 days at 21° C. Bacterial isolates which did not form clear haloes (inhibition zones) on the *E. amylovora* S435 lawns were selected for determination of transposon insertion site.

Identification Transposon Insertions Sites Using Transposon Insertion Sequencing (Tn-Seq)

Genomic DNA of 8 clones was extracted from cultures using phenol-chloroform and pooled together. DNA was sequenced at the Genome Québec Innovation Centre (McGill University, Montreal, QC). DNA concentrations were determined using the Quant-iT™ PicoGreen® dsDNA Assay Kit (Life Technologies). DNA samples were generated using the NEBNext® Ultra™ II DNA Library Prep Kit for Illumina (New England BioLabs) as per the manufacture protocol. TruSeq™ adapters and PCR primers were purchased from IDT. Size selection of libraries containing the desired insert size was obtained using SPRIselect™ beads (Beckman Coulter). Briefly, genomic DNA was fragmented and tagged with adapter sequence via one enzymatic reaction (tagmentation). Thereafter, PCR was used to amplify the region between the end of the insertion (primer TnErwinia-CS1:(5' ACACTGACGACATGGTTCTACAGCGGCCGCACTTGTGTATAA 3' (SEQ ID NO: 174) [transposon-specific sequence is in Bold])), and the Illumina adapter with primer 2 (5' TACGGTAGCAGAGACTTGGTCTCTAGCATAGAGTGCGTAGCTCTGCT 3') (SEQ ID NO: 175) to enrich for transposon insertion sites and allow multiplex sequencing. The thermocycler program was 94° C. for 2 min, 94° C. for 30 s, 55° C. for 30 s 72° C. for 30 s for 33 cycles and 72° C. for 7 min. This region was reamplified to add the Illumina adapters for MiSeg™ sequencing: PE1-CS1 (AGATCGGAAGAGCACACGTCTGAACTCCAGTCACACACTGACGACATGGTTCTACA) (SEQ ID NO: 176) and primer 2. Thereafter, sequencing was performed on an Illumina MiSeq using the MiSeq Reagent Kit v2 Kit (500-cycles). In order to find the transposon insertion sites, reads were mapped to *P. agglomerans* NY60 genome (CP034469.1).

9.2 Results

Genome Mining Studies

Genome mining of biosynthetic gene clusters (BGC) including NRPSs and other secondary metabolites were predicted using antiSMASH 5.0. The summary of the identified secondary metabolites for strains *B. velezensis* FL50S and *P. poae* FL10F are shown in Tables 14 and 15.

For the *B. velezensis* FL50S, through genome mining, a total of 14 putative BGCs were found of which, 8 were identified, including non-ribosomal peptide synthetases (NRPSs) atrributed to biosynthesis of surfactin, iturin and fengycin, and polyketide synthases (PKSs) encoding for difficidin, macrolactin and bacillaene (Table 14).

Interestingly, crude extracellular metabolite studies showed that the polyketide oxydifficidin is the major active metabolite produced by *B. velezensis* FL50S against *E. amylovora* 5435, with this extracellular metabolite fraction producing inhibition halos on a lawn of *E. amylovora* S435 that were comparable in diameter to that of the live strain itself or crude extracellular metabolites therefrom.

TABLE 14

Identified biosynthetic gene cluster regions in the genome of *B. velezensis* FL50S

| Biosynthetic gene cluster type | Most similar known cluster | Similarity | MIBiG BGC-ID |
|---|---|---|---|
| NRPS | Surfactin | 82% | BGC0000433 |
| NRPS, transAT-PKS | Fengycin | 80% | BGC0001095 |
| NRPS, transAT-PKS | Iturin | 88% | BGC0001098 |
| transAT-PKS | Difficidin | 100% | BGC0000176 |
| transAT-PKS | Macrolactin | 100% | BGC0000181 |
| transAT-PKS, NRPS | Bacillaene | 85% | BGC0001089 |
| NRPS | Bacillibactin | 100% | BGC0000309 |
| other | Bacilysin | 100% | BGC0001184 |

For the *pseudomonas* sp. FL10F, a total of 5 NRPSs gene clusters were identified. Among them, two unlinked NRPS gene clusters with 100% similarity to gene clusters coding for NRPS responsible for biosynthesis of cyclic lipopeptide (CLP) Poaeamide were identified. Crude extracellular metabolite studies showed that the cyclic lipopeptide white line-inducing principle (WLIP), a cyclic lipopeptide from Viscosin subfamily (Massetolide E, F, L or Viscosin), is the major active metabolite produced by *P. poae* FL10F against *E. amylovora* S435, with this extracellular metabolite fraction producing inhibition halos on a lawn of *E. amylovora* S435 that were comparable in diameter to that of the live strain itself or crude extracellular metabolites therefrom.

TABLE 15

Identified biosynthetic gene cluster regions in the genome of *P. poae* FL10F

| Biosynthetic gene cluster type | Most similar known cluster | Similarity | MIBiG BGC-ID |
|---|---|---|---|
| NRPS-like | Mangotoxin | 71% | BGC0000387 |
| NRPS | Poaeamide | 100% | BGC0001208 |
| NRPS | Pyochelin | 100% | BGC0000412 |
| NRPS | Poaeamide | 100% | BGC0001208 |
| NRPS | Safracin | 100% | BGC0000421 |

Mass Spectrometry Identification of Metabolites

Figure 4A:
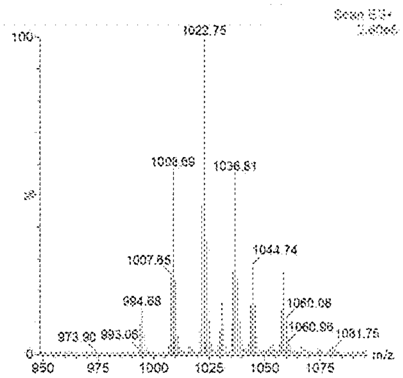
FIGS. 4A-4C show MS spectra of three families of cyclic lipopeptides produced by *B. velezensis* FL50S.
Figure 4B:
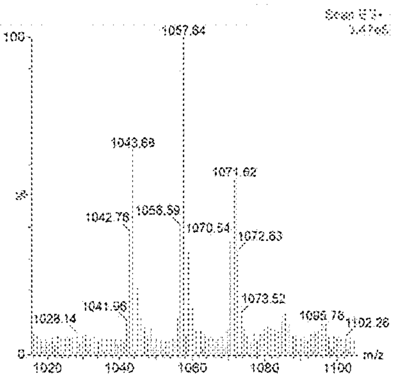
Figure 4C:
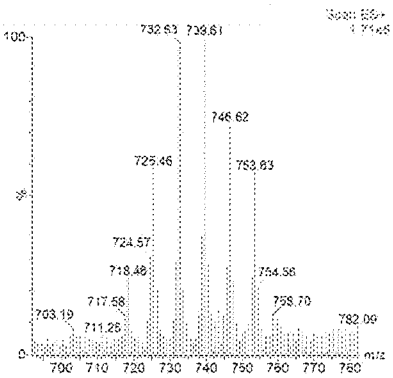
Figure 5:
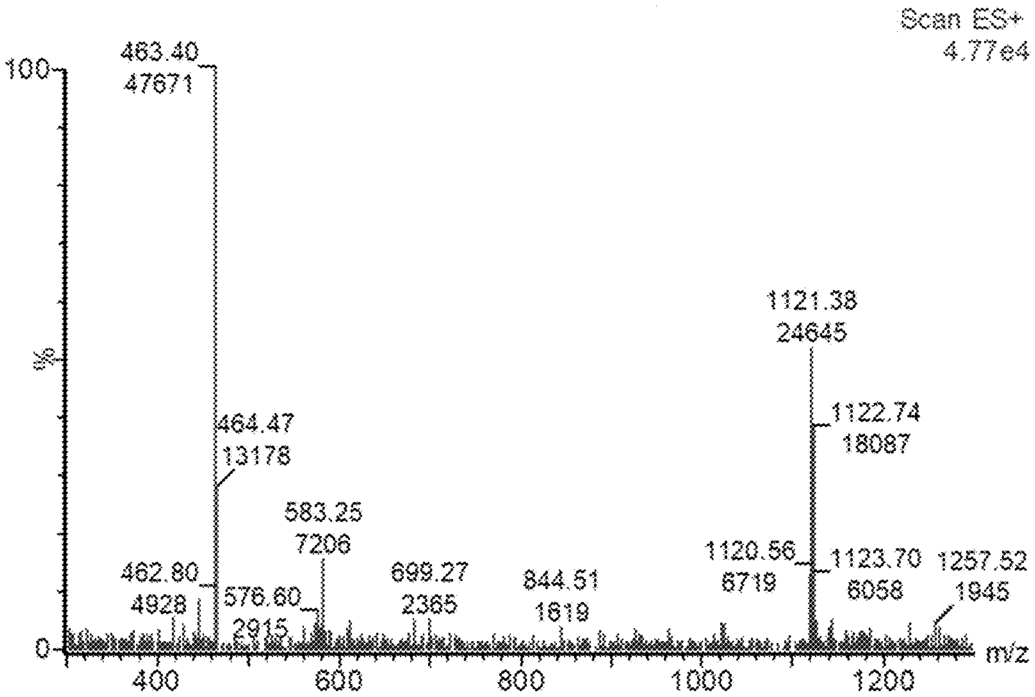
FIG. 5 shows MS spectra of produced oxydifficidin in supernatant of *Bacillus velezensis* FL50S culture detected in positive ionization mode.

The antiSMASH results suggest that *B. velezensis* FL50S has the biosynthetic machinery for the production of three classes of cyclic lipopetides as well as three polyketides. To verify the antiSMASH results and see if these gene clusters are functional, cell-free supernatant of *B. velezensis* FL50S was analysed by HPLC-ESI MS. In accordance with antiSMASH results, MS spectra of *B. velezensis* FL50S indicated that it produces three families of cyclic lipopeptides, surfactins, iturins and fengycins (FIG. 4). Regarding polyketides, only the oxidized form of difficidin, oxydifficidin, could be detected (FIG. 5). Performing the HPLC-ESI MS analyses on fractions obtained from activity guided fractionation of the crude extracellular metabolite showed that the polyketide, oxydifficidin, is the major active metabolite against *E. amylovora* S435. While it is reported that difficidin and oxydifficidin can only be detected in their deprotonated forms ($[M-H]^-$=543.4 and 559.3) in the negative ionization mode, in positive mode, oxydifficidin could be detected in its dephosphorylated (m/z 463.4) and dimmer (m/z 1121.3) states.

Figure 6:
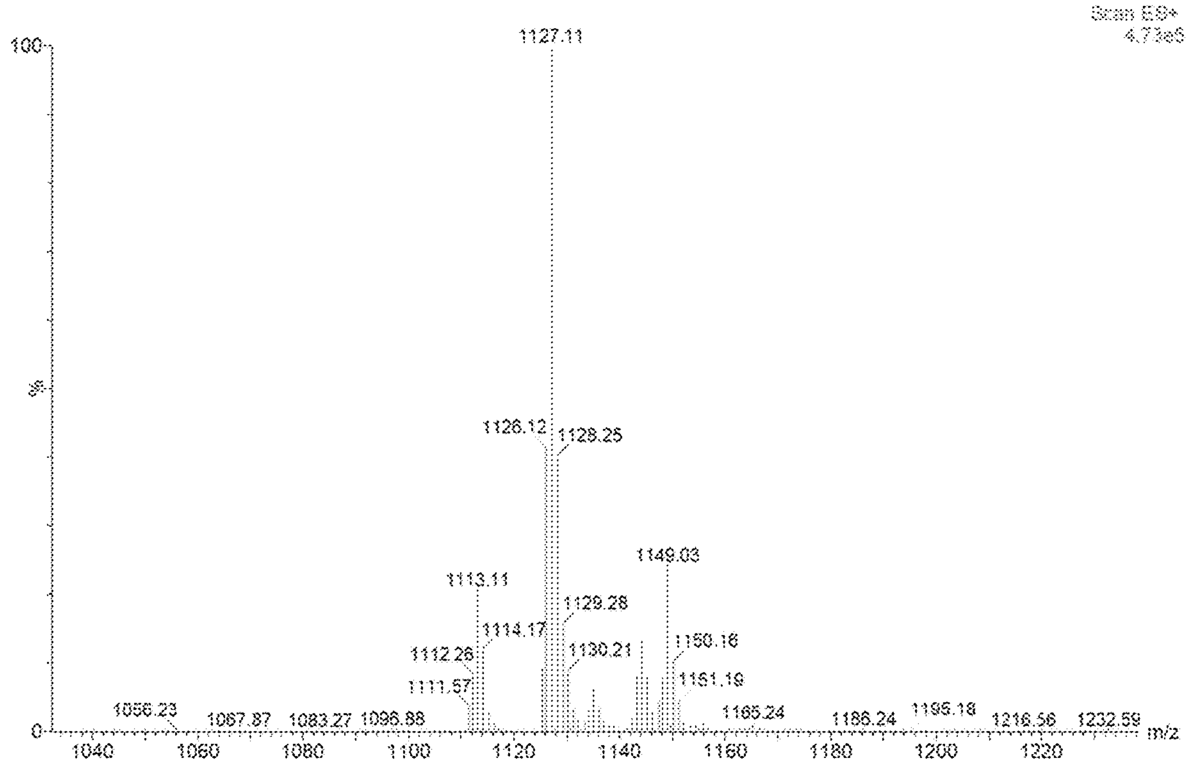
FIG. 6 shows MS spectra of fraction of *P. poae* FL active against *E. amylovora* S435.
Figure 7A:
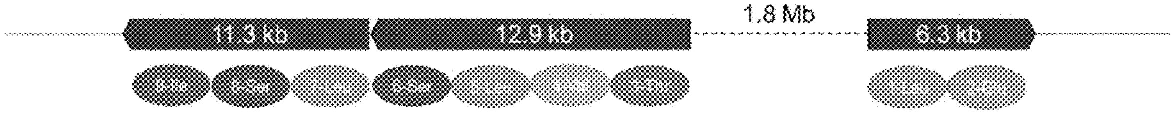
FIG. 7A shows organization of cyclic lipopeptide (CLP) biosynthetic gene clusters of *Pseudomonas poae* FL10F as identified by antiSMASH.
Figure 7B:
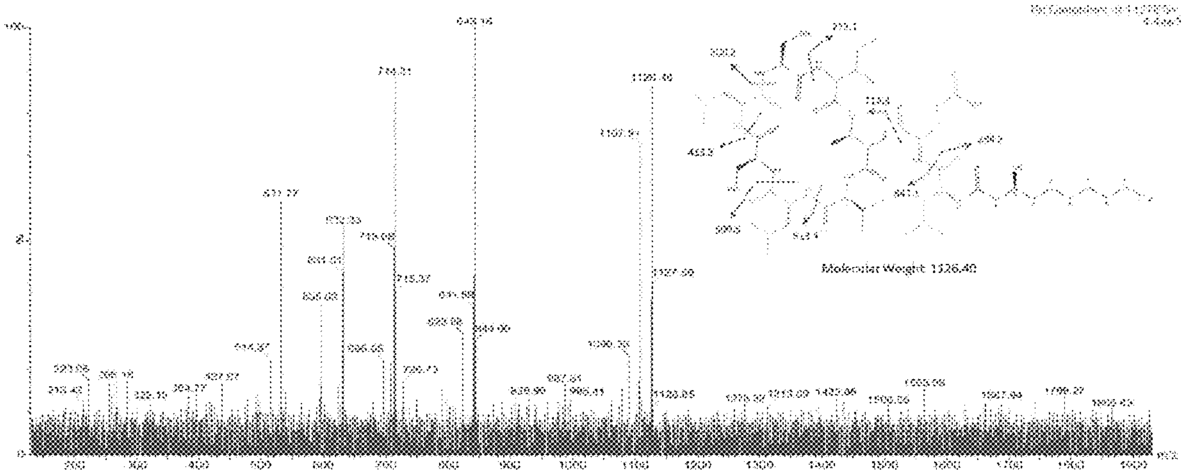
FIG. 7B shows MS/MS fragmentation spectrum of parent ion peak 1127.3 (m/z) at different collision energies in positive ionization mode. The daughter ion peaks are indicated on the proposed structure.
Figure 8:
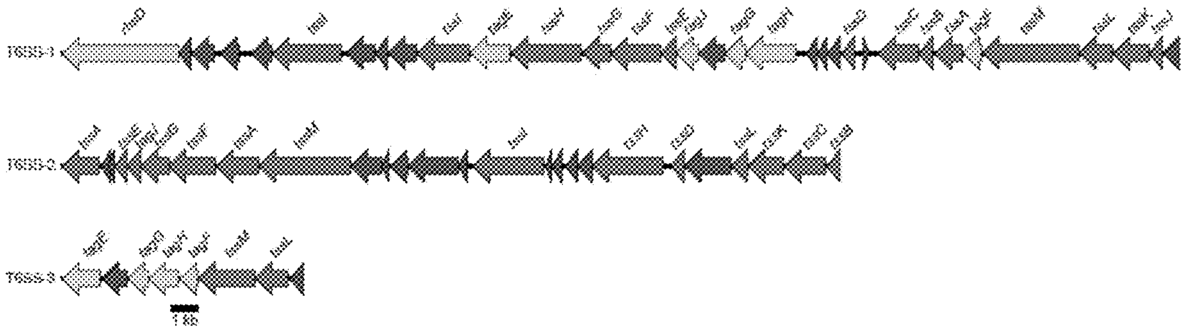
FIG. 8 shows schematic representation of the three loci with genes encoding proteins involved in T6SS found in strain *P. agglomerans* NY60. The red, green, and blue arrows represent the core, accessory, and other genes, respectively.

Analysis of the MS spectra of the active fraction of *P. poae* FL10F against *E. amylovora* S435 showed the presence of a major pseudomolecular ion peak at m/z 1127.1 and some minor peaks including 1113.1 $[M+H]^+$ with a 14 unit mass difference with the major peak (FIG. 6). Collision induced dissociation tandem MS/MS of the major pseudomolecular ion peak at m/z 1127.1, combined with antiSMASH amino acid sequence prediction of the putative product of two unlinked gene clusters coding for the cyclic lipopeptide poaeamide, suggest that 1127.1 peak could be attributed to white-line-inducing principle (WLIP), a cyclic lipopeptides from Viscosin subfamily (Massetolide E, F, L or Viscosin) (FIG. 7).

Screening for Transposon Mutants of *P. agglomerans* NY60 with Decreased Antagonist Activity Against *E. amylovora* S435

Regarding the *P. agglomerans* NY60 strain, while its cell free supernatant from nutrient broth culture showed no activity against *E. amylovora* S435, it was still able to produce an inhibition zone on lawn of *E. amylovora* S435 on TSA agar plates. This suggest that the metabolites can only be produced on solid agar medium. In order to identify the active metabolites, random transposon mutants of *P. agglomerans* NY60 were generated using mini-Tn5 Sp/Sm transposon and screened on TSA plates against streptomycin resistant *E. amylovora* S435. Transposon-generated mutants of *P. agglomerans* NY60 were screened and 8 mutants that has lost their antagonistic activity were obtained. Using transposon insertion sequencing (Tn-seq), the insertion sites in these were mapped and lead to the identification of few genes that significantly altered the production of antagonistic metabolites (Table 16).

TABLE 16

Identified transposon insertion sites in the genome of *P. agglomerans* NY60

| Insertion site | Locus tag/Gene product description |
|---|---|
| CP034469 | — |
| 474908-474967 | TonB-dependent siderophore receptor CDS |
| 569998-570191 | dndD CDS |
| 1416125-1416319 | glycosyltransferase CDS |
| 1526586-1526815 | flgL CDS |
| 4028399-4028630 | 16S rRNA |
| plasmid CP034471 | — |
| 97482-97585 | MFS transporter CDS |

Genomes of *P. agglomerans* NY60 and NY130, *P. poae* FL10F, and *B. velezensis* FL50S were determined by whole genome sequencing (Table 17).

TABLE 17

Whole genome sequencing of *P. agglomerans* NY60 and NY130, *P. poae* FL10F, and *B. velezensis* FL50S

| Strain | Genome | SEQ ID NO: |
|---|---|---|
| *P. agglomerans* | Chromosome | 14 |
| NY60 | Plasmids | 15-18 |
| *P. agglomerans* | Chromosome | 19 |
| NY130 | Plasmids | 20-23 |
| *P. poae* FL10F | Contig sequences | 24-103 |
| *B. velezensis* FL50S | Contig sequences | 104-173 |

9.2 Conclusions

*B. velezensis* FL50S

In accordance with antiSMASH results, MS spectra of *B. velezensis* FL50S indicated that it produces three families of cyclic lipopeptides, surfactins, iturins and fengycins (FIG. 4). Regarding polyketides, only the oxidized form of difficidin, oxydifficidin, could be detected (FIG. 5). Performing the HPLC-ESI MS analyses on fractions obtained from activity guided fractionation of the crude extracellular metabolite showed that the polyketide, oxydifficidin, is the major active metabolite against *E. amylovora* S435. While it is reported that difficidin and oxydifficidin can only be detected in their deprotonated forms ($[M-H]^-$=543.4 and 559.3) in the negative ionization mode, in positive mode, oxydifficidin could be detected in its dephosphorylated (m/z 463.4) and dimmer (m/z 1121.3) species.

*P. poae* FL10F

Our results demonstrate that *P. poae* FL10F produce an active extracellular compound against *E. amylovora* 5435 that can be attributed to a cyclic lipopeptide, white line-inducing principle (WLIP), a CLP from the Viscosin subfamily (Massetolide E, F, L or Viscosin).

It is interesting to note that by indexing the *Pseudomonas* specialized metabolome, in the literature, the molecular-networking-based discovery of four molecules and their evolutionary relationships were reported: a poaeamide analogue and a molecular subfamily of cyclic lipopeptides, bananamides 1, 2 and 3. Analysis of their biosynthetic gene cluster showed that it constitutes a distinct evolutionary branch of the *Pseudomonas* cyclic lipopeptides.

*P. agglomerans* NY60

The strain *P. agglomerans* NY60 had a direct cell-to-cell antagonistic effect against *E. amylovora* S435. The whole genome was sequenced by SMRT PacBio and three loci with genes known to be involved in T6SS were found. Two of the three loci include all the core genes needed to form a functional system, in addition to a few accessory genes. The third locus only harbor two core genes and is likely the remnant of an ancient T6SS locus. It is interesting to note that the three loci have important structural similarities with the T6SS-1, T6SS-2 and T6SS-3 loci found in the bacterium *P. ananatis*. However, the T6SS-2 locus is known to be plasmid-borne in *P. ananatis* while it is located on the chromosome in strain *P. agglomerans* NY60.

By screening for transposon mutants of *P. agglomerans* NY60 with decreased antagonist activity against *E. amylovora* S435, it was interestingly discovered, one of the transposons is inserted in MFS transporter gene. BLASTing the sequence indicated that it matches the sequence for EhpJ gene in *Pantoea agglomerans* (*Erwinia herbicola*) Eh1087 which is a transmembrane protein predicted to be involved in the extra cytoplasmic localization of griseoluteic acid, an intermediate in biosynthesis of broad-spectrum phenazine antibiotic D-alanylgriseoluteic acid (AGA).

Although the present invention has been described herein by way of specific embodiments thereof, it can be modified without departing from the spirit and nature of the subject invention as defined in the appended claims. The scope of the claims should not be limited by the preferred embodiments set forth in the examples but should be given the broadest interpretation consistent with the description as a whole.

REFERENCES

Fromin, N., et al., The genotypic diversity of *Pseudomonas brassicacearum* populations isolated from roots of *Arabidopsis thaliana*: influence of plant genotype. *FEMS Microbiology Ecology,* 2001. 37(1): p. 21-29.

Granatstein, D., Alternative Fire Blight Control Materials to Replace Antibiotics. 2011*, Organic Tree Fruit Industry Work Group.*

Henry D A, C. M., LiPuma J J, Speert D P., Identification of *Burkholderia cepacia* isolates from patients with cystic fibrosis and use of a simple new selective medium. *Journal of Clinical Microbiology* 1997. 35(3): p. 614-619.

Kim, I. Y., et al., Controlled release of *Pantoea agglomerans* E325 for biocontrol of fire blight disease of apple. *J Control Release,* 2012. 161(1): p. 109-15.

Lenth, R. V., Least-Squares Means: The R Package lsmeans. *Journal of Statistical Software* 2016. 69: p. 1-33.

Porter, J. N., J. J. Wilhelm, and H. D. Tresner, Method for the preferential isolation of Actinomycetes from soils. *Appl Microbiol,* 1960. 8: p. 174-8.

Pusey, P. L., et al., Antibiosis activity of *Pantoea agglomerans* biocontrol strain E325 against *Erwinia amylovora* on apple flower stigmas. *Phytopathology,* 2011. 101(10): p. 1234-41.

Smits, T. H., et al., Metabolic versatility and antibacterial metabolite biosynthesis are distinguishing genomic features of the fire blight antagonist *Pantoea vagans* C9-1. *PLoS One,* 2011. 6(7): p. e22247.

Stockwell, V. O., et al., Control of fire blight by *Pseudomonas fluorescens* A506 and *Pantoea vagans* C9-1 applied as single strains and mixed inocula. *Phytopathology,* 2010. 100(12): p. 1330-9.

All references mentioned in the present document are hereby incorporated herein by reference.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11337426B2). An electronic copy of the "Sequence Listing" will also be available from the USPTO upon request and payment of the fee set forth in 37 CFR 1.19(b)(3).

The invention claimed is:

1. A method for treating fire blight or other phytopathogenic *Erwinia* species in plants, the method comprising contacting the plant with a biopesticide comprising as an active ingredient intact or vegetative cells of a *Pantoea agglomerans* strain comprising a genomic sequence set forth in SEQ ID NO: 14 and plasmid sequences set forth in SEQ ID NOs: 15 to 18, wherein the intact or vegetative cells are formulated with glycerol and/or an agriculturally-suitable salt as a preservative.

2. The method of claim 1, wherein the biopesticide comprises phenazine produced by said *Pantoea agglomerans* strain.

3. The method of claim 1, wherein the biopesticide comprises D-alanylgriseoluteic acid (AGA) produced by said *Pantoea agglomerans* strain.

4. The method of claim 1, wherein the *Pantoea agglomerans* strain expresses the transmembrane protein EhpJ.

5. The method of claim 1, wherein the biopesticide comprises an agriculturally acceptable excipient, additive, and/or a further preservative.

6. The method of claim 1, wherein the biopesticide is formulated as a liquid, concentrate, powder, tablet, gel, pellets, granules, or any combination thereof.

7. The method of claim 1, wherein the agriculturally-suitable salt is NaCl.

8. The method of claim 7, wherein the NaCl is present in said biopesticide in a concentration of about 4% w/w.

9. The method of claim 1, wherein the glycerol is present in said biopesticide in a concentration of about 0.5% w/w.

10. The method of claim 1, wherein the biopesticide completely kills *E. amylovora* strain S435, streptomycin-resistant *E. amylovora* strain S153, and/or streptomycin-resistant *E. amylovora* strain S1605, when co-cultivated together in vitro.

11. A method for treating fire blight or other phytopathogenic *Erwinia* species in plants, the method comprising contacting the plant with a biopesticide comprising: intact or vegetative cells of a *Pantoea agglomerans* strain comprising a genomic sequence set forth in SEQ ID NO: 14 and plasmid sequences set forth in SEQ ID NOs: 15 to 18, as an active ingredient; about 0.5% glycerol w/w; and about 4% NaCl, wherein the biopesticide completely kills *E. amylovora* strain S435, streptomycin-resistant *E. amylovora* strain S153, and/or streptomycin-resistant *E. amylovora* strain S1605, when co-cultivated together in vitro.

* * * * *